United States Patent
Savord et al.

Patent Number: 6,126,602
Date of Patent: Oct. 3, 2000

[54] PHASED ARRAY ACOUSTIC SYSTEMS WITH INTRA-GROUP PROCESSORS

[75] Inventors: Bernard J. Savord; Karl E. Thiele, both of Andover, Mass.

[73] Assignee: Agilent Technologies, Inc., Palo Alto, Calif.

[21] Appl. No.: 09/398,353

[22] Filed: Sep. 17, 1999

Related U.S. Application Data

[63] Continuation of application No. 09/085,718, May 28, 1998.
[51] Int. Cl.$^7$ .................................................. A61B 8/00
[52] U.S. Cl. ................................. 600/447; 600/443
[58] Field of Search ............................. 600/447, 438, 600/448, 437, 443; 73/642

[56] References Cited

U.S. PATENT DOCUMENTS

| | | | |
|---|---|---|---|
| 5,549,111 | 8/1996 | Wright et al. | 73/642 |
| 5,797,847 | 8/1998 | Miller et al. | 600/447 |

Primary Examiner—Marvin M. Lateef
Assistant Examiner—Maulin Patel

[57] ABSTRACT

The disclosed ultrasound imaging apparatus and method use a transducer array with a very large number of transducer elements or a transducer array with many more transducer elements than beamformer channels. The imaging apparatus includes a transmit array including a multiplicity of transducer elements allocated into several transmit sub-arrays, and a receive array including a multiplicity of transducer elements allocated into several receive sub-arrays. The apparatus also includes several intra-group transmit processors, connected to the transmit sub-arrays, constructed and arranged to generate a transmit acoustic beam directed into a region of interest, and several intra-group receive processors connected to the receive sub-arrays. Each intra-group receive processor is arranged to receive, from the transducer elements of the connected sub-array, transducer signals in response to echoes from the transmit acoustic beam. Each intra-group receive processor includes delay and summing elements constructed to delay and sum the received transducer signals. The apparatus also includes a receive beamformer including several processing channels connected to the intra-group receive processors, wherein each processing channel includes a beamformer delay constructed and arranged to synthesize receive beams from the echos by delaying signals received from the intra-group receive processor, and a beamformer summer (a summing junction) constructed and arranged to receive and sum signals from the processing channels. An image generator is constructed and arranged to form an image of the region of interest based on signals received from the receive beamformer. The apparatus is practical in size, cost and complexity and is sufficiently fast to provide two-dimensional or three-dimensional images of moving body organs.

38 Claims, 21 Drawing Sheets

PHASED ARRAY ACOUSTIC SYSTEMS WITH INTRA-GROUP PROCESSORS

This application claims priority from U.S. patent application Ser. No. 09/085,718, filed May 28, 1998.

FIELD OF THE INVENTION

This invention relates to ultrasound, phased array imaging systems and, more particularly, to imaging systems that use a transducer array with a very large number of transducer elements. This invention also relates to imaging systems that include a transducer array with a larger number of transducer elements than beamformer channels.

BACKGROUND OF THE INVENTION

Phased array ultrasonic imaging systems have been used to produce real-time images of internal portions of the human body. Such imaging systems include a multiple channel transmit beamformer and a multiple channel receive beamformer either coupled to a single array of ultrasonic transducers using a transmit/receive switch, or coupled separately to a transmit transducer array and a receive transducer array. The transmit beamformer generates timed electrical pulses and applies them to the individual transducer elements in a predetermined timing sequence. The transducers respond to the electrical pulses and emit corresponding pressure waves, which are phased to form a transmit beam that propagates in a predetermined direction from the transducer array.

As the transmit beam passes through the body, a portion of the acoustic energy is scattered back toward the transducer array from tissue structures having different acoustic characteristics. An array of receive transducers (which may be the same as the transmit array) converts the pressure pulses into the corresponding electrical pulses. Due to different distances, the ultrasonic energy scattered from a tissue structure, arrives back at the individual transducers at different times. Each transducer produces an electrical signal that is amplified and provided to one processing channel of the receive beamformer. The receive beamformer has a plurality of processing channels with compensating delay elements connected to a summing element. The system selects a delay value for each channel to collect echoes scattered from a selected point. Consequently, when the delayed signals are summed, a strong signal is produced from signals corresponding to the selected point, but signals arriving from other points, corresponding to different times, have random phase relationships and thus destructively interfere. The relative delays of the compensating delay elements control the orientation of the receive beam with respect to the transducer array. Thus, the receive beamformer can steer dynamically the receive beam to have a desired direction and can focus the beam to a desired depth.

To collect imaging data, the transmit beamformer directs the transducer array to emit ultrasound beams along multiple transmit scan lines distributed over a desired scan pattern. For each transmit beam, the receive transducer array connected to the receive beamformer synthesizes one or several receive beams having selected orientations. The transmit and receive beams form a round-trip beam (i.e., "center of mass" beam) that is generated over a predetermined angular spacing to create a wedge-shaped acoustic image or is generated over a predetermined linear spacing to create a parallelogram-shaped acoustic image.

Most of the medical ultrasound imaging systems today employ a one-dimensional transducer array to form a two-dimensional image slice through a volume of interest. Increasingly, however, medical practitioners prefer three-dimensional images. To acquire three-dimensional imaging data, the ultrasound system can either use a one-dimensional transducer array that is mechanically moved in a second dimension or can use a two-dimensional transducer array. While the mechanical scanning method may provide good images, the method requires several minutes to obtain a three-dimensional data set. The organ of interest may, however, move during the data acquisition. Therefore, the use of a two-dimensional transducer array is preferred for some purposes.

The two-dimensional array (or even a one and half-dimensional transducer array used for elevation aperture control) may have several hundred to several thousand transducer elements. A basic problem with these large arrays is how to connect them to the receive beamformer, which has a limited number of signal processing channels, such as the 128 channel systems prevalent today. Several solutions were suggested.

One technique employs analog multiplexers that select groups of a reduced number of transducer elements to be connected to the beamformer. The selected group of elements is then electronically updated for each acoustic line. However, in this technique, only a small acoustic aperture is active at any time.

Another technique uses several sub-array receive processors, each connected to a group of receive elements. The sub-array processors provide their outputs to a conventional beamformer. The processors may include analog phase shifters to effectively increase the number of receive elements connectable to available beamformer channels. The use of phase shifters, however, limits the amount of effective delay available within a sub-array processor and thereby limits the number of elements within the sub-array.

Alternatively, one may try to build a beamformer with several hundred or even thousand signal processing channels and connect each channel to one transducer element. Presumably, such arrangement would be very expensive and impractical. Furthermore, this arrangement would require an impractical number of wires within the transducer cable, connecting the transducer handle containing the transducer array and the electronic box with the beamformer.

To pulse the transducer elements, a conventional ultrasound system typically uses a pulse generator for triggering the transmit elements. The pulse generator uses a synchronous counter for counting clock cycles until a desired delay value is reached, and also for counting clock cycles to give the desired pulse width and number of pulses. Since typically one synchronous counter is connected to one transducer element, a system connected to such large two-dimensional transducer array would need hundreds or thousand synchronous counters to provide transmit pulses; this would require a large amount of power and space. Furthermore, the conventional ultrasound system connected to a very large number of transducer elements would require a very large number of receive beamformer channels with delay lines having large delays and fine delay resolution.

In general, there is a need for an ultrasound imaging system that uses a large transducer array for providing two-dimensional or three-dimensional images. The system would need to be practical in size, cost and complexity and sufficiently fast to acquire images of moving organs.

SUMMARY OF THE INVENTION

The present invention relates to an ultrasound imaging apparatus or method that uses a transducer array with a large number of transducer elements and relates to an ultrasound imaging apparatus or method that uses a transducer array with many more transducer elements than beamformer channels. The apparatus is practical in size, cost and complexity and is sufficiently fast to provide two-dimensional or three-dimensional images of moving body organs.

In one aspect, a phased array acoustic apparatus for imaging a region of interest includes a transmit array including a multiplicity of transducer elements allocated into several transmit sub-arrays, and a receive array including a multiplicity of transducer elements allocated into several receive sub-arrays. The apparatus also includes several intra-group transmit processors, connected to the transmit sub-arrays, constructed and arranged to generate a transmit acoustic beam directed into a region of interest, and several intra-group receive processors connected to the receive sub-arrays. Each intra-group receive processor is arranged to receive, from the transducer elements of the connected sub-array, transducer signals in response to echoes from the transmit acoustic beam. Each intra-group receive processor includes delay and summing elements constructed to delay and sum the received transducer signals. The apparatus also includes a receive beamformer including several processing channels connected to the intra-group receive processors, wherein each processing channel includes a beamformer delay constructed and arranged to synthesize receive beams from the echos by delaying signals received from the intra-group receive processor, and a beamformer summer (a summing junction) constructed and arranged to receive and sum signals from the processing channels. An image generator is constructed and arranged to form an image of the region of interest based on signals received from the receive beamformer.

This aspect may include one or more of the following features:

The phased array acoustic apparatus includes a controller that is constructed and arranged to provide simultaneously a transmit delay profile to the intra-group transmit processors, and is constructed and arranged to provide simultaneously a receive delay profile to the intra-group receive processors. The transmit and receive delay profiles include signal delay values associated with the transmit and receive transducer elements connected to one intra-group transmit processor and one intra-group receive processor, respectively.

The phased array acoustic apparatus includes a controller constructed and arranged to provide a transmit number to each the intra-group transmit processor. The intra-group transmit processor includes at least one delay processor constructed and arranged to calculate from the transmit number transmit delay values associated with the transmit transducer elements of the intra-group transmit processor. The phased array acoustic apparatus may also include a controller constructed and arranged to provide a receive number to each intra-group receive processor. The intra-group receive processor includes at least one delay processor constructed and arranged to calculate from the receive number receive delay values associated with the receive transducer elements of the intra-group receive processor. The delay processor may be an adder.

The phased array acoustic apparatus includes a transmit beamformer including several transmit processing channels constructed and arranged to provide transmit signals to the intra-group transmit processors for controlling relative delays between the transmit sub-arrays.

The intra-group transmit processors include shift registers constructed and arranged to generate pulses with selected delay values. The intra-group transmit processors include multiplexers constructed and arranged to select one of several delay signals used to excite the transmit transducer elements. The intra-group transmit processors include both the shift registers and the multiplexers that are constructed and arranged to select and provide to the transmit transducer elements one of the pulses generated by the shift registers.

The intra-group transmit processors include programmable delay lines. The programmable delay lines include dual clock flip-flops.

The phased array acoustic apparatus includes a handle that is positionable near the region of interest and is constructed to hold the transducer elements. The handle is also constructed to accommodate the intra-group transmit processors.

The phased array acoustic apparatus includes a handle that is positionable near the region of interest and is constructed to hold the transducer elements, and includes a connector constructed to accommodate the intra-group transmit processors.

The intra-group receive processor includes several delay elements constructed to delay the transducer signals and provide the delayed transducer signals to the summing element. The intra-group receive processor includes several delay elements and several summing elements constructed to delay and sum the transducer signals.

The intra-group receive processor includes one of the following elements constructed and arranged to delay the transducer signal: a charge coupled device, an analog RAM, a sample-and-hold circuit, an active filter, an L-C filter, a switched capacitor filter.

The intra-group receive processor includes a summing delay line comprising the delay and summing elements. The intra-group receive processor also includes a cross point switch constructed and arranged to connect a signal from a receive transducer element to a selected tap of the summing delay line. The cross point switch may also constructed and arranged to connect the signal from several of the receive transducer elements to at least one of the taps of the summing delay line.

The intra-group receive processor includes a network of fixed gain amplifiers connected to a cross point switch arranged to apply a weighted gain to a provided signal and connect the weighted gain signal to at least one the tap of the summing delay line.

The intra-group receive processor includes a tapped delay line with several delay elements. The tapped delay line includes several summing elements located between the delay elements and connected to input taps. Alternatively, the tapped delay line includes several output taps located between the delay elements. The intra-group receive processor may also include a multiplexer connected to the input or output taps and arranged to select one of the taps and to provide an output connected to the processing channel of the receive beamformer. Alternatively, the intra-group receive processor may also include at least two multiplexers connected to the input or output taps, wherein the multiplexers are constructed and arranged to provide a weighted gain signal.

The phased array acoustic apparatus includes a handle positionable near the region of interest and constructed to accommodate the transducer elements, wherein the intra-group receive processors are constructed in an integrated form (i.e., one or several integrated circuits and discrete elements located, for example, on a printed-circuit board) to be placed within the handle.

The phased array acoustic apparatus includes a handle positionable near the region of interest and constructed to accommodate the transducer elements, and includes a connector constructed to accommodate the intra-group receive processors being constructed in an integrated form (i.e., one or several integrated circuits and discrete elements located, for example, on a printed-circuit board).

The intra-group receive processor may include several summing elements connected in parallel to the delay elements and arranged to receive signals from several points in the region of interest.

The receive beamformer may include several the processing channels connected in parallel to form a parallel receive beamformer. The parallel processing channels are connected to the receive intra-group processors and are constructed and arranged to synthesize several receive beams simultaneously.

In another aspect, a phased array acoustic apparatus for imaging a region of interest includes a transmit array including a multiplicity of transducer elements allocated into several transmit sub-arrays, and a receive array including a multiplicity of transducer elements connected to a receive beamformer. The apparatus also includes several intra-group transmit processors, connected to the transmit sub-arrays, constructed and arranged to generate a transmit acoustic beam directed into a region of interest. The receive beamformer includes a multiplicity of processing channels, wherein each processing channel includes a beamformer delay constructed and arranged to synthesize receive beams from the echos by delaying signals received from the transducer elements and a beamformer summer (a summing junction) constructed and arranged to receive and sum signals from the processing channels. An image generator is constructed and arranged to form an image of the region of interest based on signals received from the receive beamformer.

This aspect may include one or more of the following features:

The phased array acoustic apparatus includes a controller that is constructed and arranged to provide simultaneously a transmit delay profile to the intra-group transmit processors. The transmit delay profile includes signal delay values associated with the transmit transducer elements connected to one intra-group transmit processor.

The phased array acoustic apparatus includes a controller constructed and arranged to provide a transmit number to each the intra-group transmit processor. The intra-group transmit processor includes at least one delay processor constructed and arranged to calculate from the transmit number transmit delay values associated with the connected transmit transducer elements of the intra-group transmit processor. The delay processor may be an adder.

The phased array acoustic apparatus includes a transmit beamformer including several transmit processing channels constructed and arranged to provide transmit signals to the intra-group transmit processors for controlling relative delays between the transmit sub-arrays.

The intra-group transmit processors include shift registers constructed and arranged to generate pulses with selected delay values. The intra-group transmit processors include multiplexers constructed and arranged to select one of several delay signals used to excite the transmit transducer elements. The intra-group transmit processors include both the shift registers and the multiplexers that are constructed and arranged to select and provide to the transmit transducer elements one of the pulse trains generated by the shift registers.

The intra-group transmit processors include programmable delay lines. The programmable delay lines include dual clock flip-flops.

The phased array acoustic apparatus includes a handle that is positionable near the region of interest and is constructed to accommodate the transducer elements. The handle is also constructed to accommodate the intra-group transmit processors being constructed in an integrated form (i.e., one or several integrated circuits and discrete elements located, for example, on a printed-circuit board).

The phased array acoustic apparatus includes a handle that is positionable near the region of interest and is constructed to accommodate the transducer elements, and includes a connector constructed to accommodate the intra-group transmit processors being constructed in an integrated form (i.e., one or several integrated circuits and discrete elements located, for example, on a printed-circuit board).

In another aspect, a phased array acoustic apparatus for imaging a region of interest includes a transmit array including a multiplicity of transducer elements connected to a transmit beamformer, and a receive array including a multiplicity of transducer elements allocated into several receive sub-arrays. The transmit beamformer includes several transmit beamformer channels connected to the transducer elements and constructed and arranged to generate a transmit acoustic beam emitted into a region of interest. The apparatus includes several intra-group receive processors connected to the receive sub-arrays. Each intra-group receive processor is arranged to receive, from the transducer elements of the connected sub-array, transducer signals in response to echoes from the transmit acoustic beam. Each intra-group receive processor includes several charge coupled devices that form delay elements arranged to delay the received transducer signals, and a summing element constructed to receive and sum the delayed transducer signals. The apparatus also includes a receive beamformer including several processing channels connected to the intra-group receive processors, wherein each processing channel includes a beamformer delay constructed and arranged to synthesize receive beams from the echos by delaying signals received from the intra-group receive processor, and a beamformer summer (a summing junction) constructed and arranged to receive and sum signals from the processing channels. An image generator is constructed and arranged to form an image of the region of interest based on signals received from the receive beamformer.

This aspect may include one or more of the following features:

The phased array acoustic apparatus includes a controller constructed and arranged to provide simultaneously a receive delay profile to the intra-group receive processors. The receive delay profile includes signal delay values associated with the receive transducer elements connected to one of the intra-group receive processors.

The intra-group receive processor includes a multiplexor constructed to provide a selected clock signal of a selected frequency to the charge coupled device based on the signal delay value.

The phased array acoustic apparatus includes a controller constructed and arranged to provide a receive number to each intra-group receive processor. Each intra-group receive processor including at least one delay processor constructed and arranged to calculate from the receive number receive delay values associated with the receive transducer elements connected to the intra-group receive processor. The delay processors are adders.

The phased array acoustic apparatus includes a handle that is positionable near the region of interest and is constructed to accommodate the transducer elements. The handle is also constructed to accommodate the intra-group transmit processors being constructed in an integrated form.

The phased array acoustic apparatus includes a handle that is positionable near the region of interest and is constructed to accommodate the transducer elements, and includes a connector constructed to accommodate the intra-group transmit processors being constructed in an integrated form.

The intra-group receive processor includes several parallel summing elements connected to the charge coupled devices and arranged to receive in parallel signals from several points in the region of interest.

In another aspect, a phased array acoustic apparatus for imaging a region of interest includes a transmit array including a multiplicity of transducer elements connected to a transmit beamformer, and a receive array including a multiplicity of transducer elements allocated into several receive sub-arrays. The transmit beamformer includes several transmit beamformer channels connected to the transducer elements and constructed and arranged to generate a transmit acoustic beam emitted into a region of interest. The apparatus includes several intra-group, receive processors connected to the receive sub-arrays. Each intra-group receive processor is arranged to receive, from the transducer elements of the connected sub-array, transducer signals in response to echoes from the transmit acoustic beam. Each intra-group receive processor includes several sample-and-hold circuits that form delay elements arranged to delay the received transducer signals, and a summing element constructed to receive and sum the delayed transducer signals. The apparatus also includes a receive beamformer including several processing channels connected to the intra-group receive processors, wherein each processing channel includes a beamformer delay constructed and arranged to synthesize receive beams from the echos by delaying signals received from the intra-group receive processor, and a beamformer summer (a summing junction) constructed and arranged to receive and sum signals from the processing channels. An image generator is constructed and arranged to form an image of the region of interest based on signals received from the receive beamformer.

This aspect may include one or more of the following features:

The phased array acoustic apparatus includes a controller constructed and arranged to provide simultaneously a receive delay profile to the intra-group receive processors. The receive delay profile includes signal delay values associated with the receive transducer elements connected to one of the intra-group receive processors.

The intra-group receive processor includes a multiplexor constructed to provide a selected clock signal to the sample-and-hold circuits to obtain a selected delay value.

The phased array acoustic apparatus includes a controller constructed and arranged to provide a receive number to each intra-group receive processor. Each intra-group receive processor including at least one delay processor constructed and arranged to calculate from the receive number receive delay values associated with the receive transducer elements connected to the intra-group receive processor. The delay processors are adders.

The intra-group receive processor includes the sample-and-hold circuits and several the summing elements arranged to form a summing delay line. The intra-group receive processor also includes a cross point switch constructed and arranged to connect a signal from the receive transducer element to a selected tap of the summing delay line. The cross point switch is constructed and arranged to connect the signal from several of the receive transducer elements to at least one of the taps of the summing delay line. The intra-group receive processor includes a network of fixed gain amplifiers connected to the cross point switch, wherein the network and the cross point switch are arranged to apply a weighted gain to the signal and connect the weighted gain signal to at least one the tap of the summing delay line.

The intra-group receive processor includes the sample-and-hold circuits arranged to form a tapped delay line with input taps. The tapped delay line includes summing elements connected to the input taps and located between the sample-and-hold circuits. The intra-group receive processor may include a multiplexer connected to the input taps and arranged to select one of the input taps. Alternatively, the intra-group receive processor may include at least two multiplexers connected to the input taps, wherein the multiplexers are constructed and arranged to provide a weighted gain signal.

The intra-group receive processor includes the sample-and-hold circuits arranged to form a tapped delay line with output taps. The intra-group receive processor may include a multiplexer connected to the output taps and arranged to select one of the output taps and provide an output connected to the processing channel of the receive beamformer. Alternatively, the intra-group receive processor may include at least two multiplexers connected to the output taps, wherein the multiplexers are constructed and arranged to provide a weighted gain signal from the output taps.

The phased array acoustic apparatus includes a handle that is positionable near the region of interest and is constructed to accommodate the transducer elements. The handle is also constructed to accommodate the intra-group transmit processors being constructed in an integrated form.

The phased array acoustic apparatus includes a handle that is positionable near the region of interest and is constructed to accommodate the transducer elements, and includes a connector constructed to accommodate the intra-group transmit processors being constructed in an integrated form.

The intra-group receive processor includes several parallel summing elements connected to the sample-and-hold circuits and arranged to receive in parallel signals from several points in the region of interest.

In another aspect, a phased array acoustic apparatus for imaging a region of interest includes a transmit array including a multiplicity of transducer elements connected to a transmit beamformer, and a receive array including a multiplicity of transducer elements allocated into several receive sub-arrays. The transmit beamformer includes several transmit beamformer channels connected to the transducer elements and constructed and arranged to generate a transmit acoustic beam emitted into a region of interest. The apparatus includes several intra-group receive processors connected to the receive sub-arrays. Each intra-group receive processor is arranged to receive, from the transducer elements of the connected sub-array, transducer signals in response to echoes from the transmit acoustic beam. Each intra-group receive processor includes several analog RAM elements that form delay elements arranged to delay the received transducer signals, and a summing element constructed to receive and sum the delayed transducer signals.

The apparatus also includes a receive beamformer including several processing channels connected to the intra-group receive processors, wherein each processing channel includes a beamformer delay constructed and arranged to synthesize receive beams from the echos by delaying signals received from the intra-group receive processor, and a beamformer summer (a summing junction) constructed and arranged to receive and sum signals from the processing channels. An image generator is constructed and arranged to form an image of the region of interest based on signals received from the receive beamformer.

This aspect may include one or more of the following features:

The phased array acoustic apparatus includes a controller constructed and arranged to provide simultaneously a receive delay profile to the intra-group receive processors. The receive delay profile includes signal delay values associated with the receive transducer elements connected to one of the intra-group receive processors.

The intra-group receive processor includes a multiplexor constructed to provide a selected clock signal to the analog RAM elements to obtain a selected delay of the transducer signal.

The phased array acoustic apparatus includes a controller constructed and arranged to provide a receive number to each intra-group receive processor. Each intra-group receive processor including at least one delay processor constructed and arranged to calculate from the receive number receive delay values associated with the receive transducer elements connected to the intra-group receive processor. The delay processors are adders.

The intra-group receive processor includes the analog RAM elements and several the summing elements arranged to form a summing delay line. The intra-group receive processor also includes a cross point switch constructed and arranged to connect a signal from the receive transducer element to a selected tap of the summing delay line. The cross point switch is constructed and arranged to connect the signal from several of the receive transducer elements to at least one the taps of the summing delay line. The intra-group receive processor includes a network of fixed gain amplifiers connected to the cross point switch, wherein the network and the cross point switch are arranged to apply a weighted gain to the signal and connect the weighted gain signal to at least one the tap of the summing delay line.

The intra-group receive processor includes the analog RAM elements arranged to form a tapped delay line with input taps. The tapped delay line includes several summing elements connected to the input taps located between the analog RAM elements. The intra-group receive processor may include a multiplexer connected to the input taps and arranged to select one of the input taps. Alternatively, the intra-group receive processor may include at least two multiplexers connected to the input taps, wherein the multiplexers are constructed and arranged to provide a weighted gain signal from the taps.

The intra-group receive processor includes the analog RAM elements arranged to form a tapped delay line With output taps. The tapped delay line includes several output taps located between the analog RAM elements. The intra-group receive processor may include a multiplexer connected to the output taps and arranged to select one of the output taps and provide an output connected to the processing channel of the receive beamformer. Alternatively, the intra-group receive processor may include at least two multiplexers connected to the output taps, wherein the multiplexers are constructed and arranged to provide a weighted gain signal from the output taps.

The phased array acoustic apparatus includes a handle that is positionable near the region of interest and is constructed to accommodate the transducer elements. The handle is also constructed to accommodate the intra-group transmit processors being constructed in an integrated form.

The phased array acoustic apparatus includes a handle that is positionable near the region of interest and is constructed to accommodate the transducer elements, and includes a connector constructed to accommodate the intra-group transmit processors being constructed in an integrated form.

The intra-group receive processor includes several parallel summing elements connected to the analog RAM elements and arranged to receive in parallel signals from several points in the region of interest.

In another aspect, a phased array acoustic apparatus for imaging a region of interest includes a transmit array including a multiplicity of transducer elements connected to a transmit beamformer, and a receive array including a multiplicity of transducer elements allocated into several receive sub-arrays. The transmit beamformer includes several transmit beamformer channels connected to the transducer elements and constructed and arranged to generate a transmit acoustic beam emitted into a region of interest. The apparatus includes several intra-group receive processors connected to the receive sub-arrays. Each intra-group receive processor is arranged to receive, from the transducer elements of the connected sub-array, transducer signals in response to echoes from the transmit acoustic beam. Each intra-group receive processor includes several active analog filter circuits that form delay elements arranged to delay the received transducer signals, and a summing element constructed to receive and sum the delayed transducer signals. The apparatus also includes a receive beamformer including several processing channels connected to the intra-group receive processors, wherein each processing channel includes a beamformer delay constructed and arranged to synthesize receive beams from the echos by delaying signals received from the intra-group receive processor, and a beamformer summer (a summing junction) constructed and arranged to receive and sum signals from the processing channels. An image generator is constructed and arranged to form an image of the region of interest based on signals received from the receive beamformer.

In another aspect, a phased array acoustic apparatus for imaging a region of interest includes a transmit array including a multiplicity of transducer elements connected to a transmit beamformer, and a receive array including a multiplicity of transducer elements allocated into several receive sub-arrays. The transmit beamformer includes several transmit beamformer channels connected to the transducer elements and constructed and arranged to generate a transmit acoustic beam emitted into a region of interest. The apparatus includes several intra-group receive processors connected to the receive sub-arrays. Each intra-group receive processor is arranged to receive, from the transducer elements of the connected sub-array, transducer signals in response to echoes from the transmit acoustic beam. Each intra-group receive processor includes several switched capacitor filter circuits that form delay elements arranged to delay the received transducer signals, and a summing element constructed to receive and sum the delayed transducer signals. The apparatus also includes a receive beamformer including several processing channels connected to the intra-group receive processors, wherein each processing channel includes a beamformer delay constructed and arranged to synthesize receive beams from the echos by delaying signals received from the intra-group receive processor, and a beamformer summer (a summing junction) constructed and arranged to receive and sum signals from the processing channels. An image generator is constructed and arranged to form an image of the region of interest based on signals received from the receive beamformer.

The above two aspects may include one or more of the following features:

The phased array acoustic apparatus includes a controller constructed and arranged to provide simultaneously a receive delay profile to the intra-group receive processors. The receive delay profile includes signal delay values associated with the receive transducer elements connected to one of the intra-group receive processors.

The intra-group receive processor includes a multiplexor constructed to provide a selected switching signal to the active analog filter circuits to obtain a selected delay of the transducer signal.

The phased array acoustic apparatus includes a controller constructed and arranged to provide a receive number to each intra-group receive processor. Each intra-group receive processor including at least one delay processor constructed and arranged to calculate from the receive number receive delay values associated with the receive transducer elements connected to the intra-group receive processor. The delay processors are adders.

The intra-group receive processor includes the active analog filter circuits, or the switched capacitor filter circuits, and several the summing elements arranged to form a summing delay line. The intra-group receive processor also includes a cross point switch constructed and arranged to connect a signal from the receive transducer element to a selected tap of the summing delay line. The cross point switch is constructed and arranged to connect the signal from several of the receive transducer elements to at least one the taps of the summing delay line. The intra-group receive processor includes a network of fixed gain amplifiers connected to the cross point switch, wherein the network and the cross point switch are arranged to apply a weighted gain to the signal and connect the weighted gain signal to at least one the tap of the summing delay line.

The intra-group receive processor includes the active analog filter circuits or the switched capacitor filter circuits arranged to form a tapped delay line with input taps. The tapped delay line includes several summing elements connected to the input taps located between the active analog filter circuits or the switched capacitor filter circuits. The intra-group receive processor may include a multiplexer connected to the input taps and arranged to select one of the input taps. Alternatively, the intra-group receive processor may include at least two multiplexers connected to the input taps, wherein the multiplexers are constructed and arranged to provide a weighted gain signal from the output.

The intra-group receive processor includes the active analog filter circuits or the switched capacitor filter circuits arranged to form a tapped delay line with output taps.

The intra-group receive processor may include a multiplexer connected to the output taps and arranged to select one of the output taps and provide an output connected to the processing channel of the receive beamformer. Alternatively, the intra-group receive processor may include at least two multiplexers connected to the output taps, wherein the multiplexers are constructed and arranged to provide a weighted gain signal from the output taps.

The phased array acoustic apparatus includes a handle that is positionable near the region of interest and is constructed to accommodate the transducer elements. The handle is also constructed to accommodate the intra-group transmit processors being constructed in an integrated form.

The phased array acoustic apparatus includes a handle that is positionable near the region of interest and is constructed to accommodate the transducer elements, and includes a connector constructed to accommodate the intra-group transmit processors being constructed in an integrated form.

The intra-group receive processor includes several parallel summing elements connected to the active analog filter circuits or the switched capacitor filter circuits and arranged to receive in parallel signals from several points in the region of interest.

In another aspect, a method for imaging a region of interest including the steps of providing a transmit array including a multiplicity of transducer elements allocated into several transmit sub-arrays that are connected to several intra-group transmit processors, generating by the intra-group transmit processors a transmit acoustic beam of a selected direction, and emitting the transmit acoustic beam from the transmit array into a region of interest. The imaging method also includes steps of providing a receive array including a multiplicity of transducer elements allocated into several receive sub-arrays that are connected to several intra-group receive processors including delay and summing elements, providing a receive beamformer including several processing channels, connected to the several intra-group receive processors and a beamformer summer, detecting by the transducer elements echoes from the transmit acoustic beam and providing received transducer signals to the intra-group receive processors, delaying and summing the transducer signals provided from one receive sub-array to one intra-group receive processor and providing the delayed and summed signals from the intra-group receive processor to one of the beamformer channel, synthesizing receive beams in the beamformer channels based on signals from the intra-group receive processors, and forming an image of the region based on signals received from the receive beamformer.

In another aspect, a method for imaging a region of interest including the steps of providing a transmit array including a multiplicity of transducer elements allocated into several transmit sub-arrays that are connected to several intra-group transmit processors, generating by the intra-group transmit processors a transmit acoustic beam of a selected direction, and emitting the transmit acoustic beam from the transmit array into a region of interest. The imaging method also includes steps of providing a receive array including a multiplicity of transducer elements connected to a receive beamformer, detecting by the transducer elements echoes from the transmit acoustic beam and providing received transducer signals to the beamformer channels, synthesizing receive beams in the beamformer channels by applying selected delays to the transducer signals and summing the delayed signals, and forming an image of the region based on signals received from the receive beamformer.

In another aspect, a method for imaging a region of interest including the steps of providing a transmit array including a multiplicity of transducer elements connected to a transmit beamformer, generating a transmit acoustic beam, and emitting the acoustic beam into a region of interest. The imaging method also includes the steps of providing a receive array including a multiplicity of transducer elements allocated into several receive sub-arrays that are connected to several intra-group receive processors including delay and summing elements, providing a receive beamformer including several processing channels, connected to the several intra-group receive processors and a beamformer summer, detecting by the transducer elements echoes from the transmit acoustic beam and providing received transducer signals to the intra-group receive processors, delaying and summing the transducer signals provided from one receive sub-array to one intra-group receive processor and providing the delayed and summed signals from the intra-group receive processor to one of the beamformer channel, synthesizing receive beams in the beamformer channels based on signals from the intra-group receive processors, and forming an image of the region based on signals received from the receive beamformer.

DETAILED DESCRIPTION OF PREFERRED EMBODIMENTS

Figure 1:
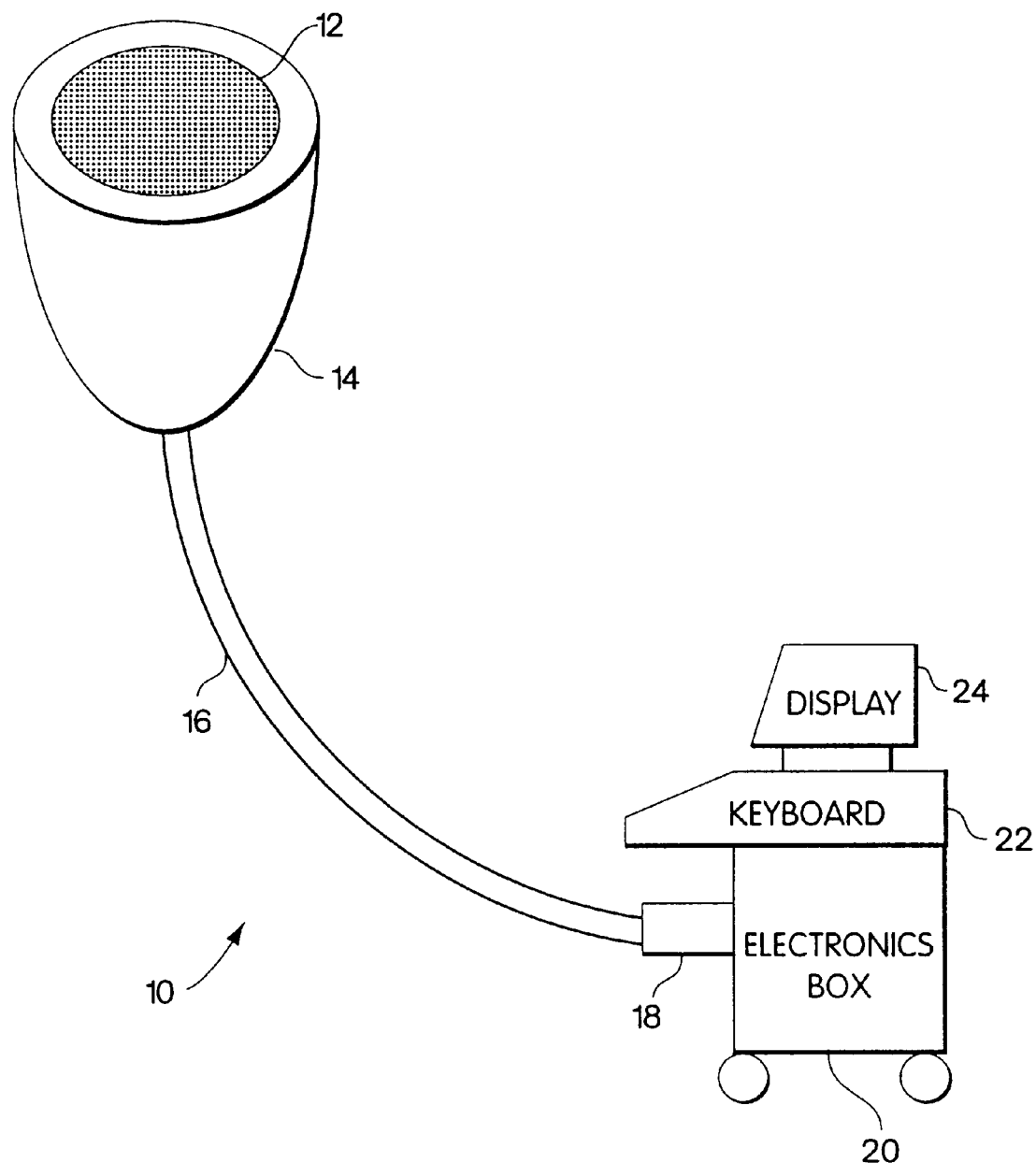
FIG. 1 illustrates a phased array ultrasound imaging system.

Referring to FIG. 1, a phased array ultrasonic imaging system 10 includes an array of transducer elements 12 located in a transducer handle 14. Transducer handle 14 is connected via a transducer cable 16 and a transducer connector 18 to an electronics box 20. Electronics box 20 is interfaced with a keyboard 22 and provides imaging signals to a display 24. Transducer array 12 includes several hundred or even several thousand transducer elements arranged as a two-dimensional array, a large one-dimensional array or a 1.5 dimensional array. Transducer array 12 may have the transducer elements arranged into separate transmit and receive arrays distributed over a selected area (e.g., a circle, an annular pattern). Alternatively, the transducer elements are distributed over a semi-random pattern. Transducer handle 14 includes transmit pulse generators and the associated high voltage drivers, low noise receive pre-amplifiers, and delay and summing circuits. Importantly, in one preferred embodiment, the elements are integrated within a small volume and placed inside transducer handle 14. Transducer cable 16 includes signal wires, power supply wires, clock lines, and serial digital data lines including a digital control line and an analog reference current line.

Alternatively, transducer array 12 employs the same transducer elements to emit a transmit beam and detect a receive beam. In this arrangement, imaging system 10 includes a transmit/receive switch (T/R switch not shown in FIG. 1) to switch between a transmit beamformer and a receive beamformer depending on the operating mode. The T/R switch includes N individual switches connected to the N transducer elements. During transmission of ultrasound energy, the switches connect the elements to the transmit beamformer and protect the receive beamformer. After emitting the transmit beam, the T/R switch connects the transducer elements to the receive beamformer.

Figure 1A:
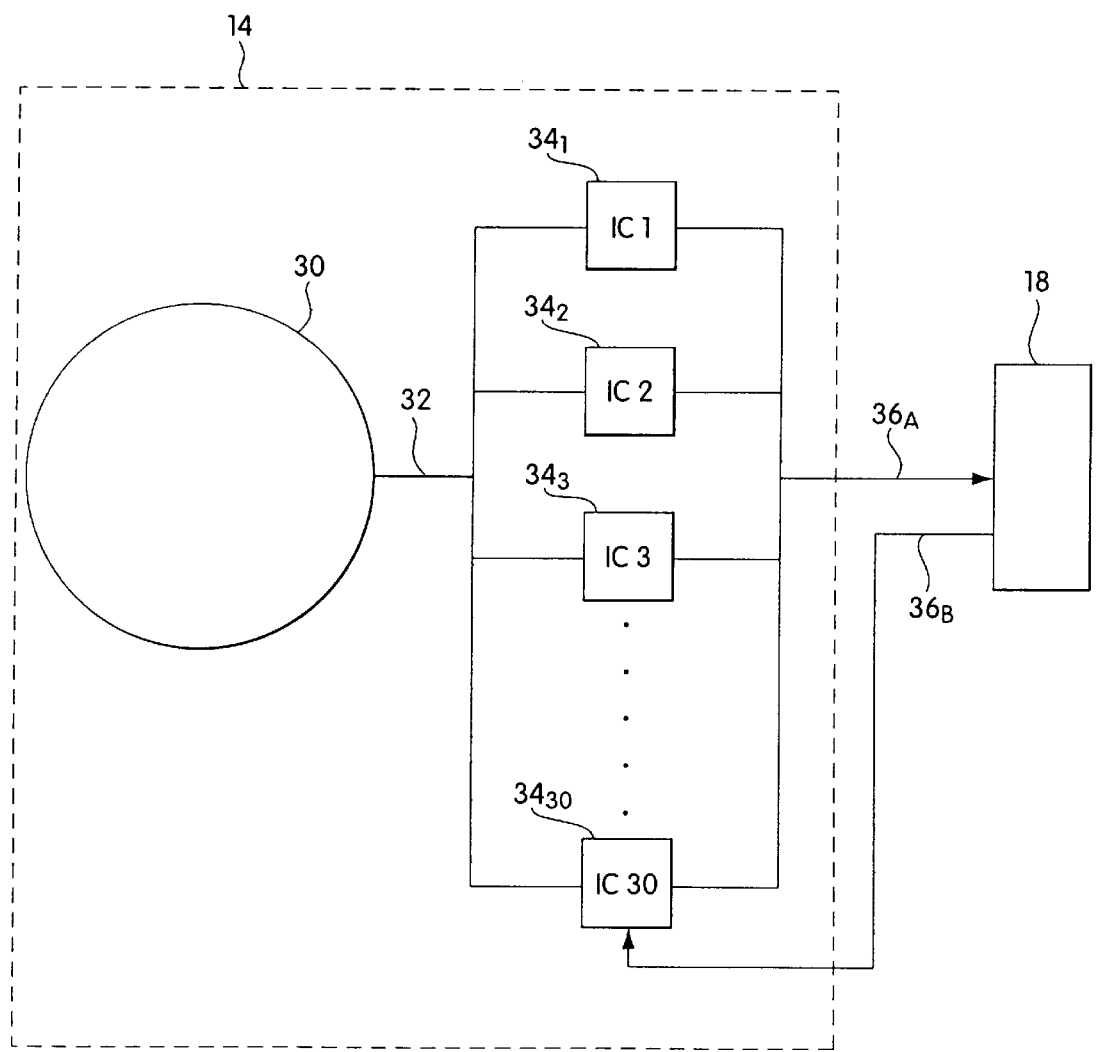
FIG. 1A shows diagrammatically a two-dimensional transducer array and the corresponding electronics integrated into a handle of the imaging system of FIG. 1.

Referring to FIG. 1A, in another preferred embodiment, ultrasound imaging system 10 utilizes two-dimensional transducer array 30 having, for example, 3,000 transducer elements to acquire three-dimensional image data of a human organ of interest. Transducer array 30 groups 3,000 transducer elements into 120 sub-arrays, each group including 5×5=25 elements. Imaging system 10 uses approximately one half of the transducer elements to transmit ultrasound energy and the other half to receive ultrasound energy. The transmit and receive elements are randomly distributed over array 30. By separating the transmit and receive elements, the system does not need the T/R switch; this reduces the complexity of the system.

Furthermore, imaging system 10 eliminates the need to use 3,000 conductors in transducer cable 16 (FIG. 1), which would be impractically large, bulky and inflexible. Transducer handle 14 includes 120 sub-arrays connected to 30 integrated circuits $34_1, 34_2, \ldots, 34_{20}$ by 3000 connections 32. Transducer cable 16 includes 120 output wires (all labeled 36A) providing outputs from the integrated circuits and includes 24 control and power supply wires (all labeled 36B). Each integrated circuit 34 may include a set of digital pulse generators that generate a 200 nsec wide transmit pulse and high voltage driver circuits that amplify the transmit pulse to 170 volts used to excite the transducer element to emit ultrasound. Each integrated circuit may also include low noise receive preamplifiers, an analog delay circuitry to perform the intra-group receive beamforming, and a digital control circuitry. The low noise receive preamplifiers preamplify the transducer signal and provide the preamplified signal to the delay circuitry that performs intra-group receive beamforming by applying selected delay values to the signals. The total power dissipated by the transmit and receive intra-group elements is under 2 Watts.

Figure 2:
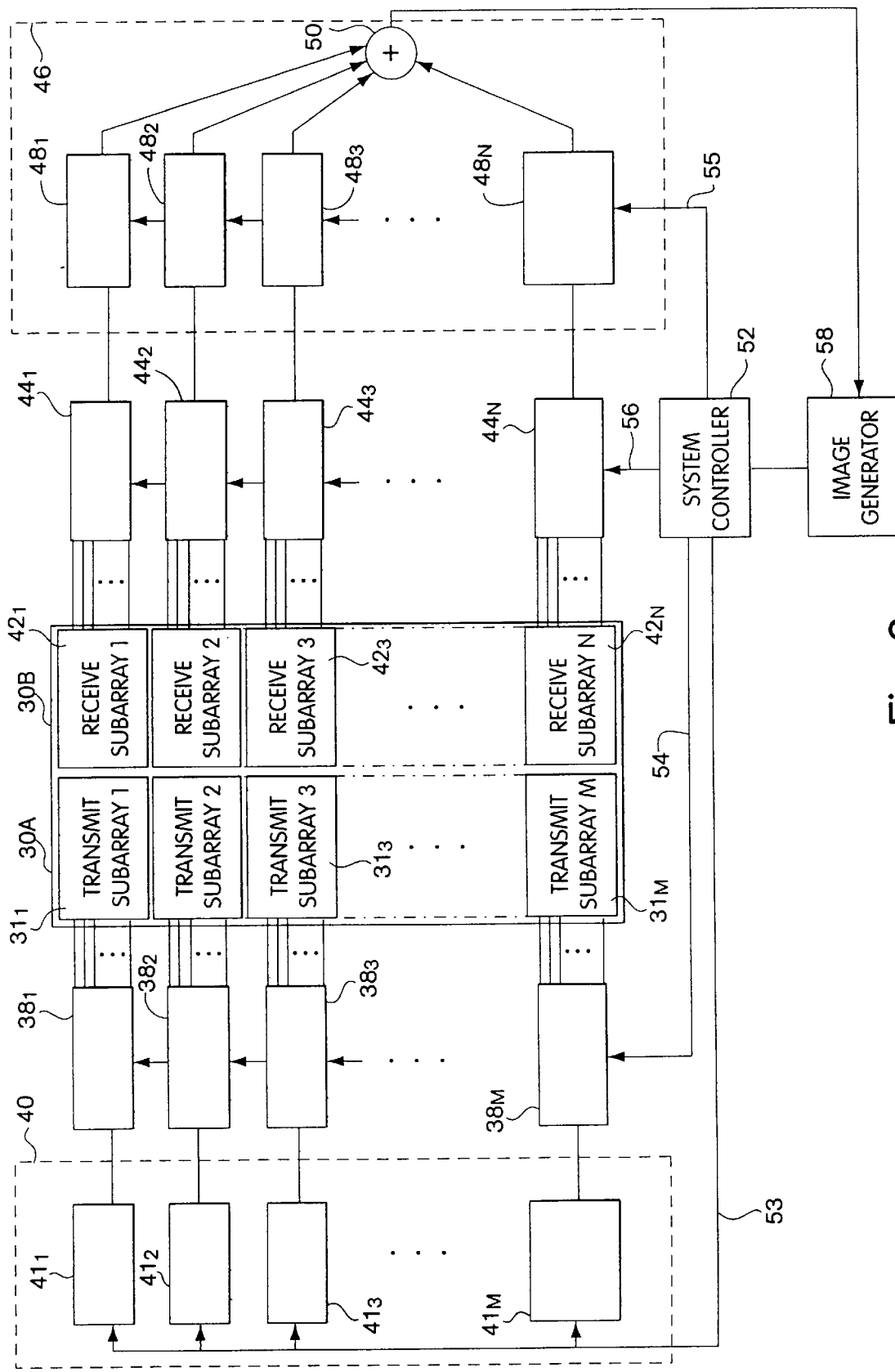
FIG. 2 shows diagrammatically the imaging system with an array of ultrasound transducers connected to several intra-group transmit and receive processors.

FIG. 2 is a block diagram of imaging system 10 having transducer array 30 (FIG. 1A) divided into M transmit sub-arrays 30A connected to M intra-group transmit processors and N receive sub-arrays 30B connected to N intra-group receive processors. Specifically, transmit sub-arrays $31_1, 31_2, \ldots, 31_M$ are connected to intra-group transmit processors $38_1, 38_2, \ldots, 38_M$, respectively, which in turn are connected to channels $41_1, 41_2, \ldots, 41_M$ of a transmit beamformer 40. Receive sub-arrays $42_1, 42_2, \ldots, 42_N$ are connected to intra-group receive processors $44_1, 44_2, \ldots, 44_N$, respectively, which, in turn, are connected to processing channels $48_1, 48_2, \ldots, 48_N$ of a receive beamformer 46. As discussed in connection with FIGS. 3 and 3A, each intra-group transmit processor $38_i$ includes one or more digital pulse generators that provide the transmit pulses and one or more voltage drivers that amplify the transmit pulses to excite the connected transducer elements. Alternatively, each intra-group transmit processor 38*i* includes a programmable delay line receiving a signal from a conventional transmit beamformer. For example, transmit outputs from ultrasound system HP Sonos 5500 are connected to the intra-group transmit processors instead of the transducer elements.

As described in connection with FIGS. 6 and 7, each intra-group receive processor $44_i$ may include a summing delay line, or several programmable delay elements connected to a summing element (a summing junction). Intra-group receive processor $44_i$ delays the individual transducer signals, adds the delayed signals, and provides the summed signal to one channel $48_i$ of receive beamformer 46. Alternatively, one intra-group receive processor provides the summed signal to several processing channels $48_i$ of a parallel receive beamformer. The parallel receive beamformer is constructed to synthesize several receive beams simultaneously. Each intra-group receive processor $44_i$ may also include several summing delay lines (or groups of programmable delay elements with each group connected to a summing junction) for receiving signals from several points simultaneously.

A system controller 52 includes a microprocessor and an associated memory and is designed to control the operation of imaging system 10. System controller 52 provides delay commands to the transmit beamformer channels via a bus 53 and also provides delay commands to the intra-group transmit processors via a bus 54. The delay data steers and focuses the generated transmit beams over transmit scan lines of a wedge-shaped transmit pattern, a parallelogram-shaped transmit pattern, or other patterns including three-dimensional transmit patterns.

A system controller 52 also provides delay commands to the channels of the receive beamformer via a bus 55 and delay commands to the intra-group receive processors via a bus 56. The applied relative delays control the steering and focussing of the synthesized receive beams. Each receive beamformer channel $48_i$ includes a variable gain amplifier, which controls gain as a function of received signal depth, and a delay element that delays acoustic data to achieve beam steering and dynamic focusing of the synthesized beam. A summing element 50 receives the outputs from beamformer channels $48_1, 48_2, \ldots, 48_N$ and adds the outputs to provide the resulting beamformer signal to an image generator 58. The beamformer signal represents a receive ultrasound beam synthesized along a receive scan line. Image generator 58 constructs an image of a region probed by a multiplicity of round-trip beams synthesized over a sector-shaped pattern, a parallelogram-shaped pattern or other patterns including three-dimensional patterns.

Both the transmit and receive beamformers may be analog or digital beamformers as described, for example, in U.S. Pat. Nos. 4,140,022; 5,469,851; or 5,345,426 all of which are incorporated by reference.

Figure 3:
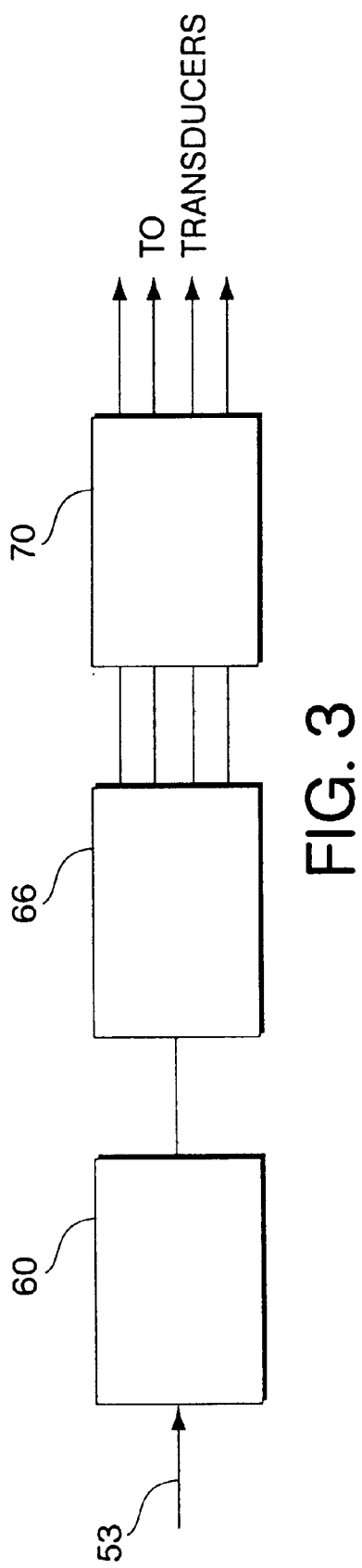
FIGS. 3 and 3A show diagrammatically different embodiments of a transmit beamformer channel connected to a transmit intra-group processor shown in FIG. 2.
Figure 3A:
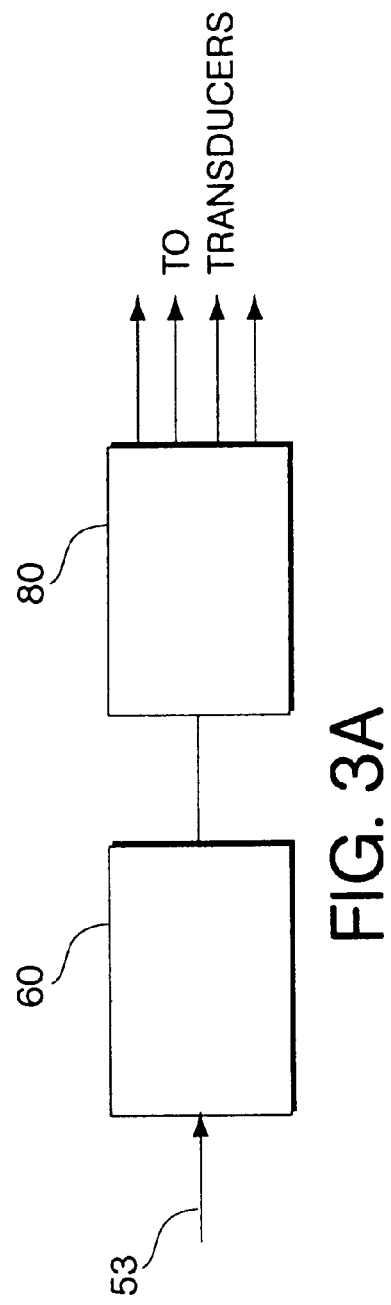

The system controller controls the timing of the transducer elements by employing "coarse" delay values in transmit beamformer channels $41_i$ and "fine" delay values in intra-group transmit processors $38_i$. There are several ways to generate the transmit pulses for the transducer elements. As shown in FIG. 3, a pulse generator 60 may provide pulse delay signals to a shift register 66, which provides several delay values to a transmit circuit 70. Transmit circuit 70 provides high voltage pulses for driving the transmit transducer elements. Alternatively, as shown in FIG. 3A, a pulse generator 60 may provide pulse delay signals to a delay line 80 connected to a transmit circuit. The delay line provides delay values to the transmit circuit, which provides high voltage pulses for driving the transmit transducer elements.

Figure 4:
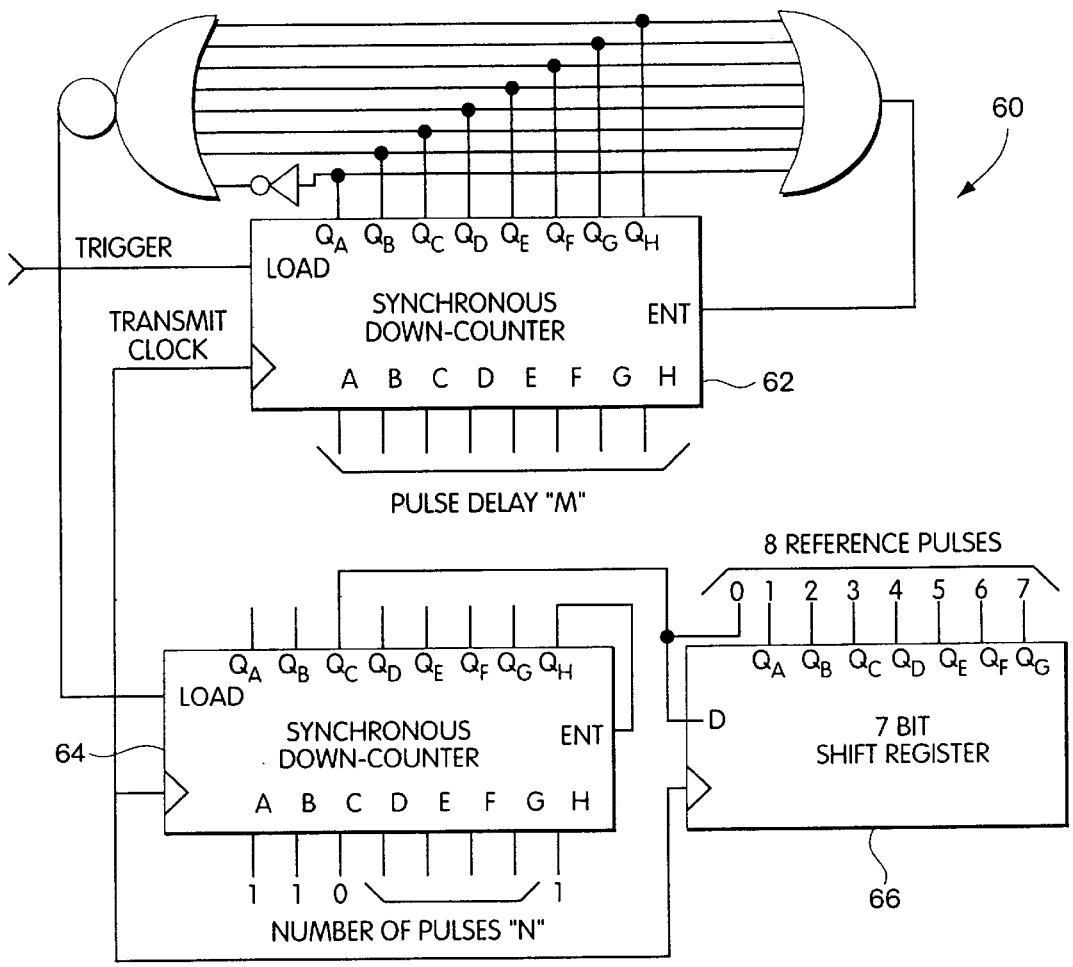
FIG. 4 shows schematically a digital pulse generator used in the embodiments of FIGS. 3 and 3A.
Figure 4A:
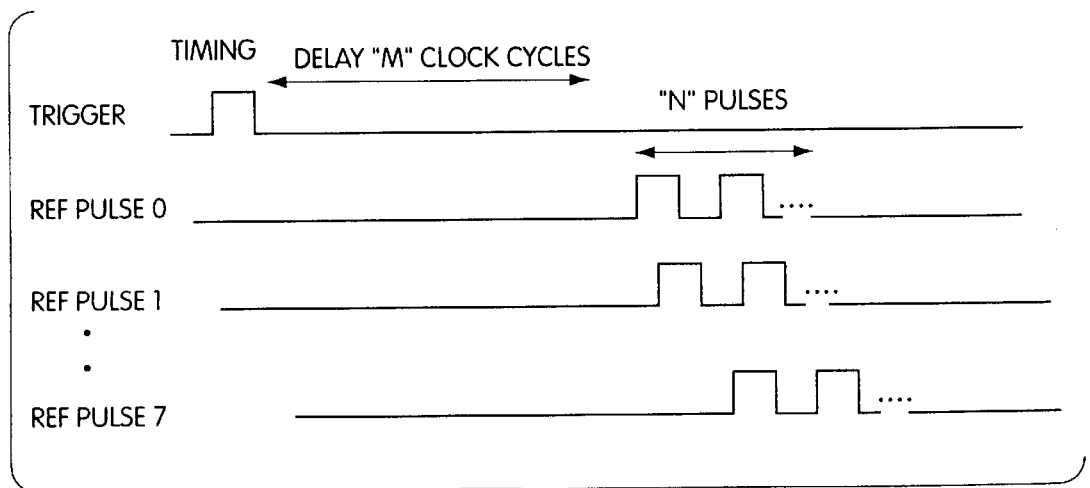
FIG. 4A is a timing diagram showing the reference pulses generated by the digital pulse generator of FIG. 4.

Referring to FIG. 4, digital pulse generator 60 includes synchronous counters 62 and 64. Synchronous counter 62 provides the pulse delay "M", and synchronous counter 64 counts clock cycles for the number "N" of transmit pulses and their width. A 7 bit shift register 66 provides seven reference pulses with seven delay values that are needed to generate eight different versions of the pulse train each having eight different delay values. FIG. 4A is a timing diagram showing the pulse delay M relative to the transmit trigger, which changes from one sub-array to another depending on the steering angle of the transmit beam. The number of transmit pulses N depends on the transmit mode. In B-mode imaging, a single pulse is transmitted for each transmit event, while in Doppler imaging several pulses are usually transmitted for each transmit event.

Figure 4B:
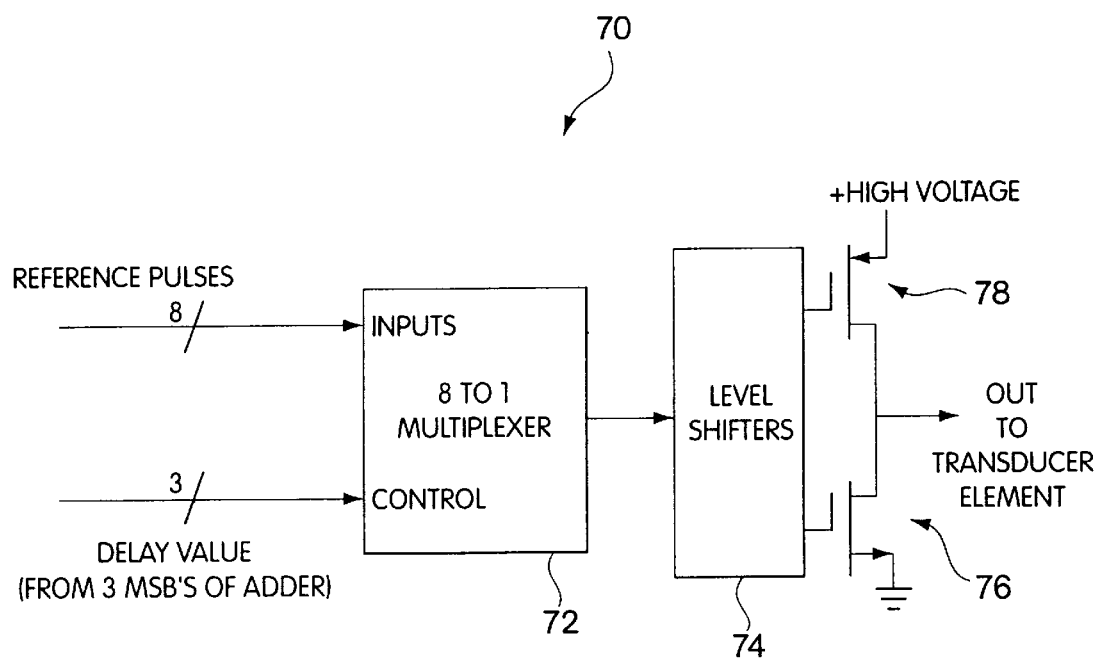
FIG. 4B shows diagrammatically a transmit circuit used with the digital pulse generator of FIG. 4.

Shift register 66 provides the reference pulses to transmit circuit 70, shown in FIG. 4B. Transmit circuit 70 includes a multiplexer 72 and a high voltage driver with level shifters 74 and transmit driver transistors 76 and 78. Multiplexer 72 receives eight reference transmit pulses from the shift register 66. Based on a provided delay value, multiplexer 72 selects one of the reference pulses and provides the selected reference pulse to level shifters 74. Level shifters 74, in turn, provide the signal to transmit driver transistors 76 and 78 for driving a transmit element of transducer array 30A (FIG. 2). Multiplexer 72 replaces seven digital pulse generators having synchronous counters, used in prior art systems. Since multiplexers consume less power and take less area than synchronous counters, the intra-group transmit processors using transmit circuits 70 consume less power and occupy a smaller area. Therefore, the intra-group transmit processors or even the entire transmit beamformer can be integrated into transducer handle 14 or connector 18, both of which provide only a limited amount of space for electronic elements and limited ability to dissipate power.

Figure 5:
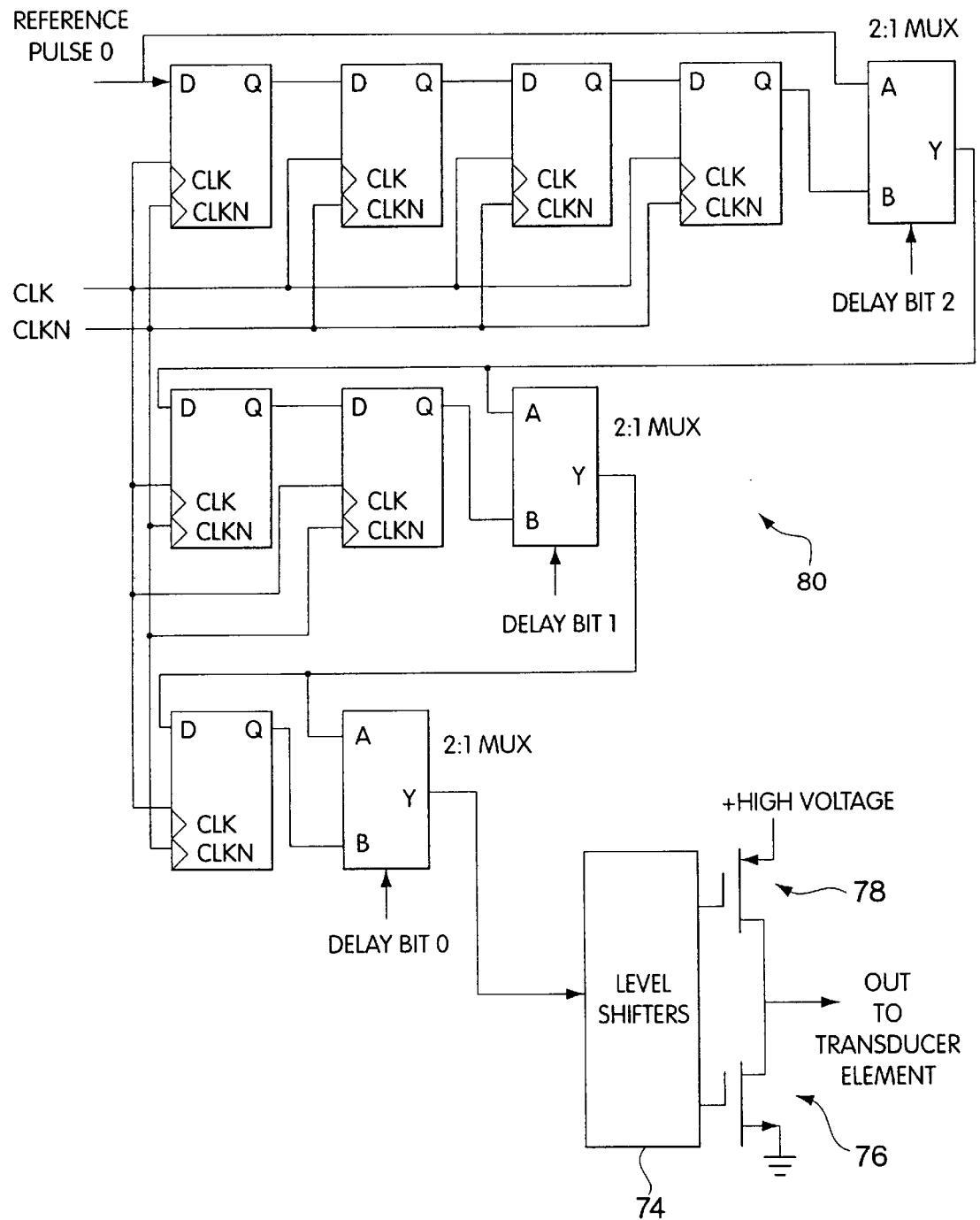
FIG. 5 shows schematically a programmable delay line made from flip-flop circuits.
Figure 5A:
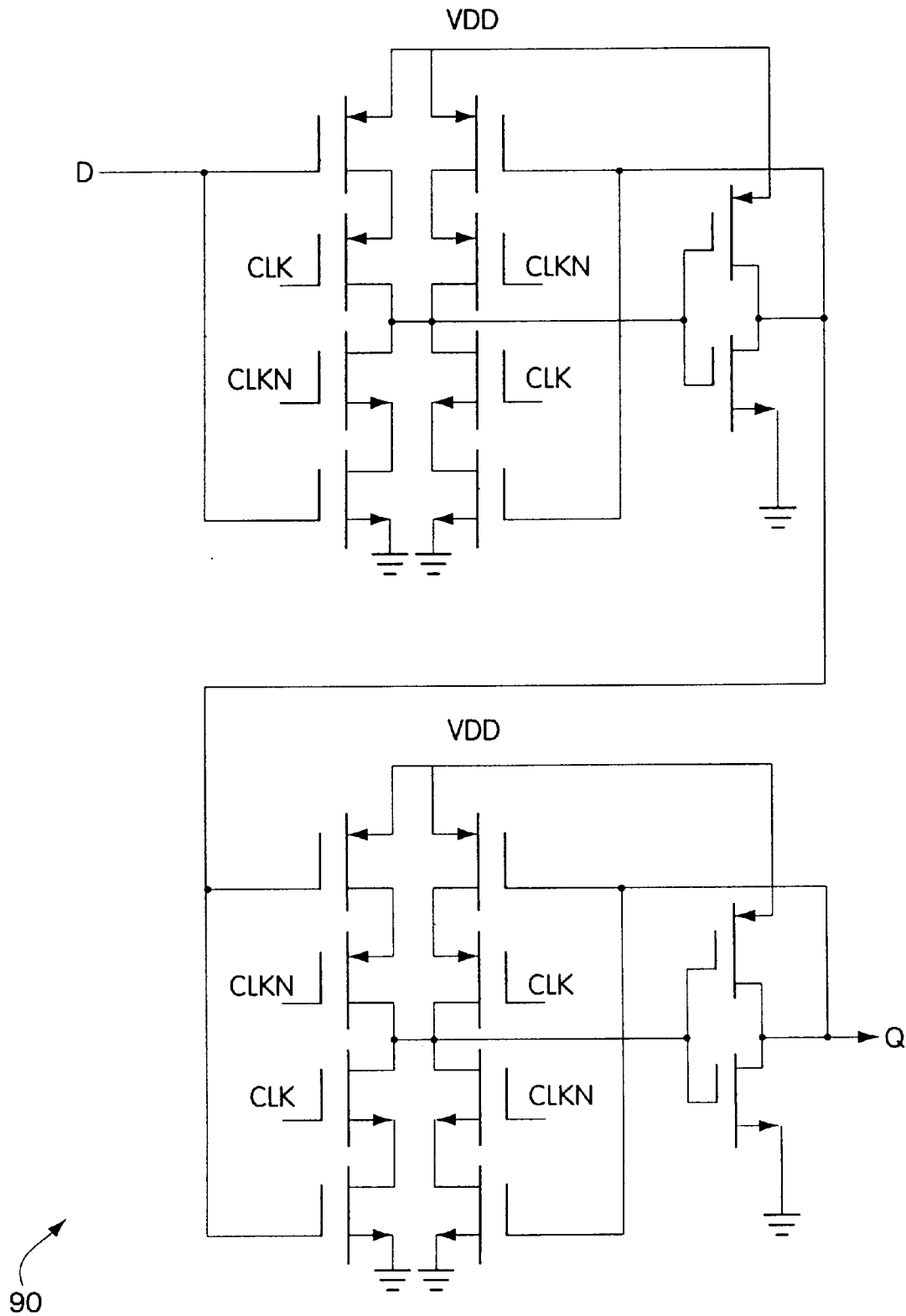
FIG. 5A shows schematically a dual clock flip-flop used in the programmable delay line of FIG. 5.

Alternatively, pulse generator 60 is connected to a programmable delay line 80 shown in FIG. 5. Programmable delay line 80 is integrated for each intra-group transmit processor. In general, a programmable delay line takes less area than the synchronous counters, but does not consume less power. To save power, programmable delay line 80 includes a dual clock flip-flop circuit 90, shown in FIG. 5A. Dual clock flip-flop circuit 90 uses 2 complementary clocks. If the output state is not changed, no current is drawn from Vdd even when the clocks are active. All the power dissipation associated with clocking the D flip-flop occurs in the clock driver circuits, which can be placed outside of transducer handle 14 to prevent overheating. Another use of dual clock flip-flops 90 is within the synchronous counters to reduce their power dissipation.

Figure 6:
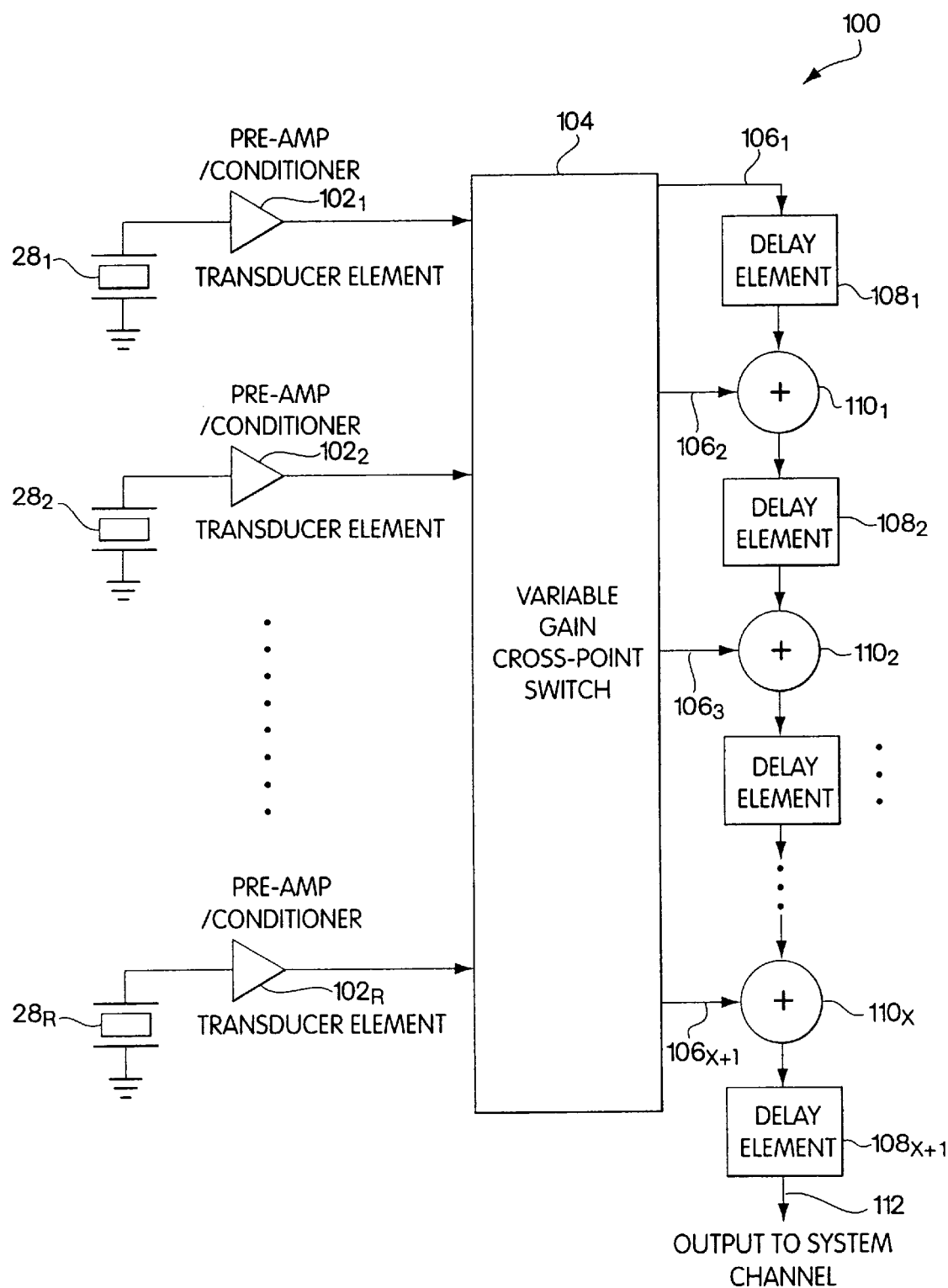
FIG. 6 is a block diagram of a summing delay line used in the intra-group receive processors of FIG. 2.
Figure 7:
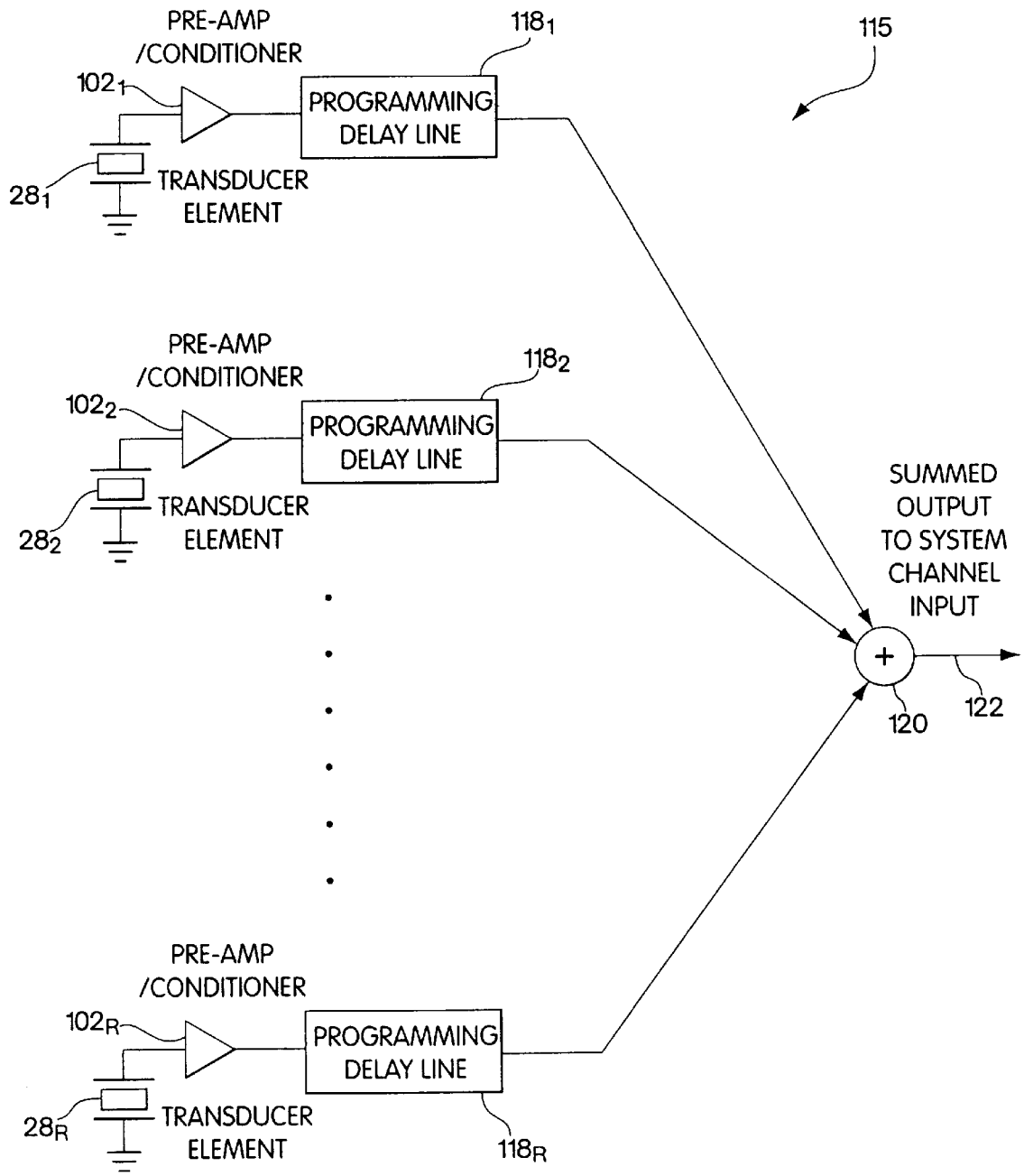
FIG. 7 is a block diagram of programmable delay lines connected to a summing junction used in the intra-group receive processors of FIG. 2.

FIGS. 6 and 7 show different embodiments of intra-group receive processors $44_1$, $44_2$, . . . , $44_N$ (shown in FIG. 2). Referring to FIG. 6, a summing delay line 100 receives signals from receive transducers $28_1$, $28_2$, . . . , $28_R$, which form one sub-array 42, of transducer array 30B. Summing delay line 100 includes a variable cross point switch 104 connected to delay elements $108_1$, $108_2$, . . . , $108_{x+1}$ and summing elements (summing junctions) $110_1$, $110_2$, . . . , $110_x$. Each receive transducer $28_i$ provides a signal to a preamplifier / conditioner $102_i$, and the preamplified signal is then steered by variable cross point switch 104 to one selected tap $106_i$ or simultaneously to several selected taps $106_i$. Thus, summing delay line 100 enables interpolation of the transducer signals between taps $106_i$ to achieve a fine control over the delay applied to the preamplified transducer signals. That is, the transducer signal can be weighted by two different gains and sent into two taps $106_i$; this achieves a delay smaller than the delay provided by a single delay element. This type of interpolation can use linear weights (i.e., the amplitude of the weighted signals add up to 1), or non-linear weights that give the same signal amplitude as would be obtained using a single delay value.

Summing delay line 100 can also provide delay values larger than the delay values provided by analog delay elements $108_1$, $108_2$, . . . , $108_{x+1}$ by programming a delay value that is an integer number of wavelengths from the desired delay value. Alternatively, to obtain larger delays (or smaller delays) than delays provided by delay elements $108_1$, $108_2$, . . . , $108_{x+1}$, analog phase shifters are included to add a phase shift to the signal to provide the needed difference in delay. Delay element $108_i$ may be a sample-and-hold element, an active filter element, or a switched capacitor filter, all of which are discussed below. Preamplifier and conditioner 102 may include a T/R switch, a pre-amplifier or a variable gain amplifier. Output 112 from the last delay element is coupled to one processing channel $48_i$ of receive beamformer 46.

Referring to FIG. 7, in another embodiment, an intra-group analog receive processor 115 includes a set of programmable delay lines $118_1$, $118_2$ and $118_R$ connected to a summing element 120. From an output 122, summing element 120 provides the delayed and summed signals to one processing channel $48_i$ of receive beamformer 46. Each programmable delay line $118_i$ may be implemented as an analog delay line or a digital delay line. Each analog delay line $118_i$ can include a charge coupled device, an analog RAM, a sample and hold circuit, an active filter, an L-C filters, or a switched capacitor filter as is described in connection with FIGS. 8 through 13.

Figure 8:
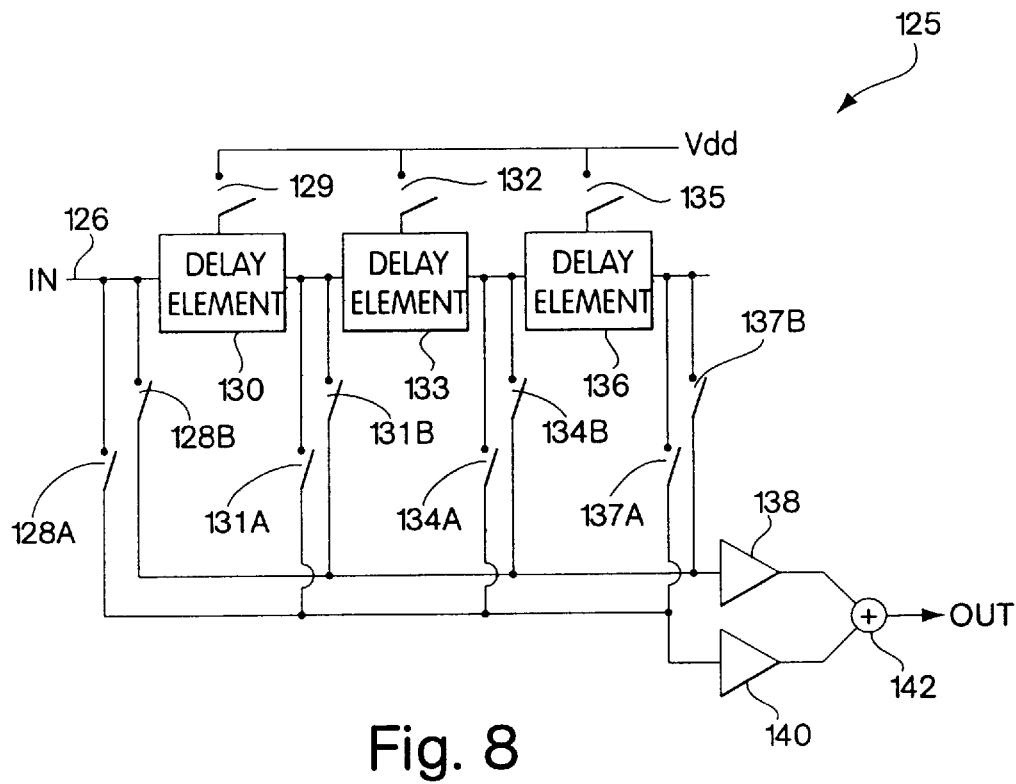
FIGS. 8 and 8A show diagrammatically tapped delay lines with output taps and input taps, respectively, used as programmable delays.
Figure 8A:
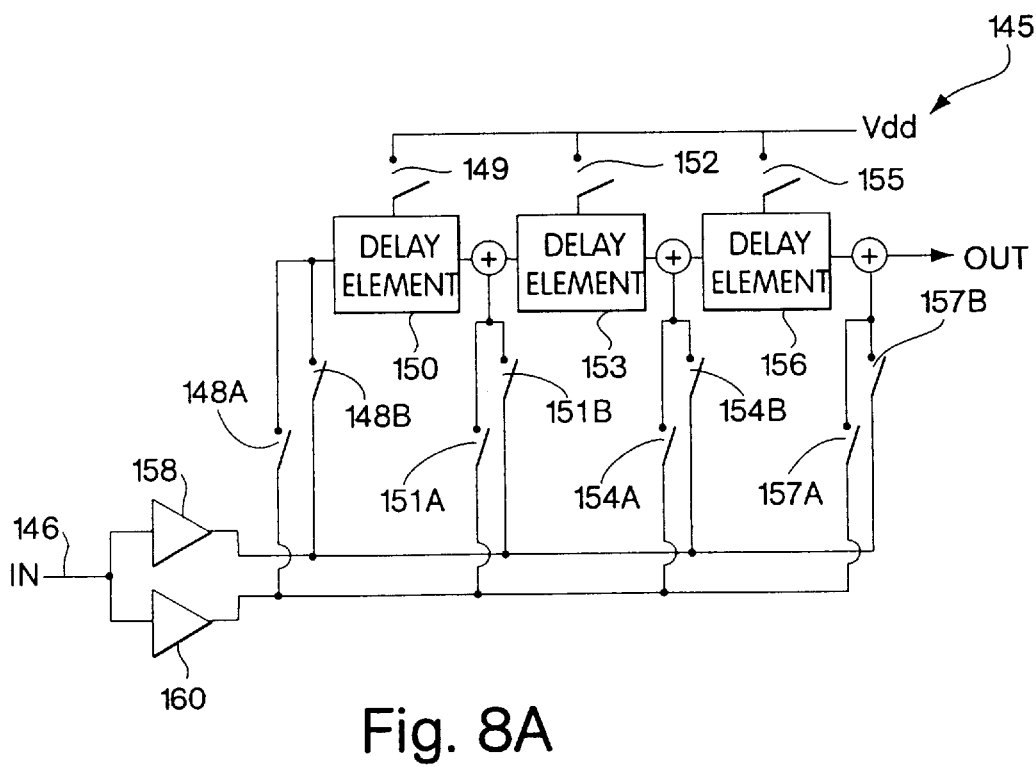

Referring to FIGS. 8 and 8A, the programmable delay line (shown in FIG. 7) may include a delay line 125 with output taps, or a delay line 145 with input taps, respectively. Delay line 125 includes three fixed delay elements 130, 133, and 136 connected by eight switches (128A, 128B, 131A, 131B, 134A, 134B, 137A and 137B) to two fix gain attenuators 138 and 140. Fixed gain attenuators 138 and 140 are connected to a summing junction 142. Delay elements 130, 133 and 136 are connected to a power supply Vdd by switches 129, 132 and 135, respectively. Switches 129, 132 and 135 are used to turn off the Vdd power supply from the unused delays to save power. Fix gain attenuators 138 and 140 in combination with output switches 128A, 128B, 131A, 131B, 134A, 134B, 137A and 137B allow interpolation of delay values and give finer delay control than the delay provided by a single delay element 130, 133 or 136. Each delay element can again be a filter element or a sample-and-hold delay element. For example, delay line 125 includes fix gain attenuator 138 providing 0.7 gain and fix gain attenuator 140 providing 0.3 gain. Each delay element 130, 133 or 136 provides a 90 degree phase shift. An ON/OFF combination of switches 128A, 128B, 131A, 131B, 134A, 134B, 137A and 137B will provide a signal with a desired delay.

Delay line 145 includes three fixed delay elements 150, 153 and 156 connected by eight input switches (148A, 148B, 151A, 151B, 154A, 154B, 157A and 157B) to two fix gain attenuators 158 and 160. Delay elements 150, 153 and 156 are connected to a power supply Vdd by switches 149, 152 and 155, respectively. Switches 149, 152 and 155 are used to turn off the Vdd power supply from the unused delays to save power. Fixed gain attenuators 158 and 160 in combination with input switches 148A, 148B, 151A, 151B, 154A, 154B, 157A and 157B allow interpolation of delay values and give finer delay control than the delay provided by a single delay element 150, 153 or 156. Each delay element can again be a filter element or a sample-and-hold delay element.

Figure 9:
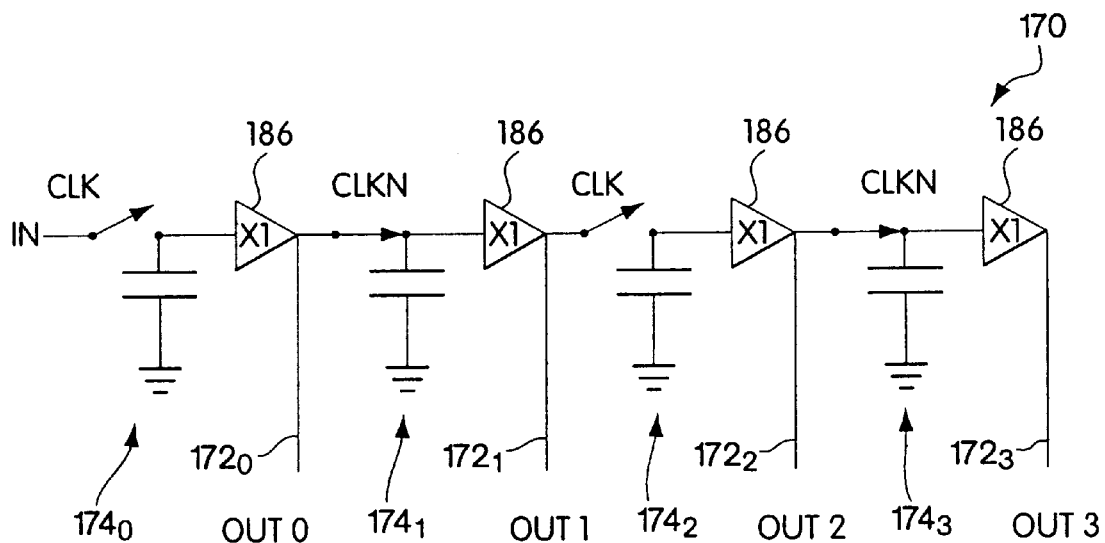
FIGS. 9 and 9A show diagrammatically sampler lines with output taps and input taps, respectively, used as programmable delays.
Figure 10C:
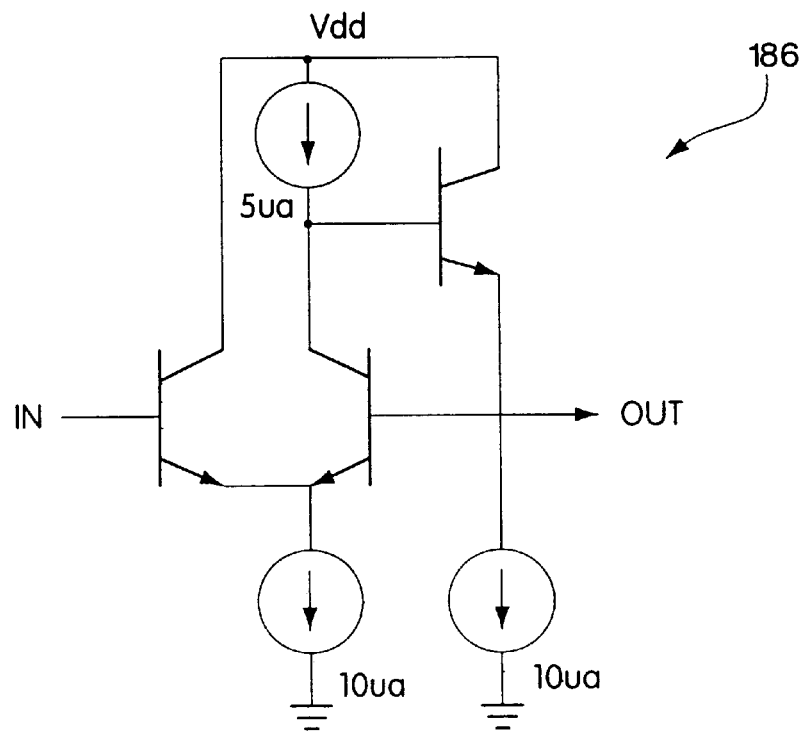
FIG. 10C is a schematic diagram of a unity gain buffer used in the embodiments of FIGS. 9, 9A, 10, 10A and 10B.
Figure 9A:
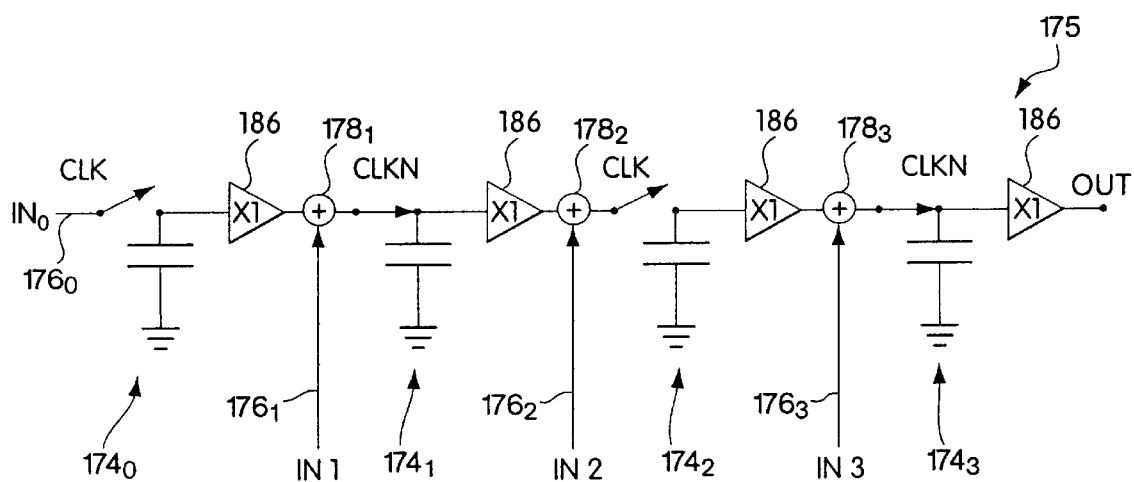

FIGS. 9 and 9A show diagrammatically sampler chains with output taps and input taps, respectively, used in the intra-group receive processors of FIG. 2. Sampler line 170, shown in FIG. 9, includes a series of sample-and-hold elements $174_0$, $174_1$, . . . , $174_3$ and a series of outputs $172_0$, $172_1$, . . . , $172_3$ controlled by a digital clock. Between two samplers there is a unity gain buffer 186 shown in FIG. 10C. The sample clock frequency is at least twice the highest signal frequency component in order to meet the Nyquist criteria. To support bandwidths up to 100%, the clock frequency is 4 times the ultrasound RF center frequency. This allows control of output delay value for every 1/18 of the RF period quantization. For example, for a 2.5 MHz ultrasound signal, sampler line 170 uses a 10 MHz clock frequency and has 4 stages to achieve a 200 nsec delay with 50 nsec taps.

Sampler line 175, shown in FIG. 9A, includes a series of samplers $174_0$, $174_1$, . . . , $174_3$ and a series of inputs $176_0$, $176_1$, . . . , $176_3$ controlled by a digital clock. A unity gain buffer 186 is located between two sample-and-hold elements. Signals provided by inputs $176_1$, $176_2$, and $176_3$ are summed into the line by summing elements $178_1$, $178_2$, and $178_3$. Again, the sample clock frequency is at least twice the highest signal frequency component in order to meet the Nyquist criteria. Sampler lines 170 or 175 are used as delay line $118_i$ of FIG. 7. Alternatively, sample-and-hold elements $174_i$ together with summing elements $178_i$ are used as summing delay line 100 shown in FIG. 6.

Figure 10:
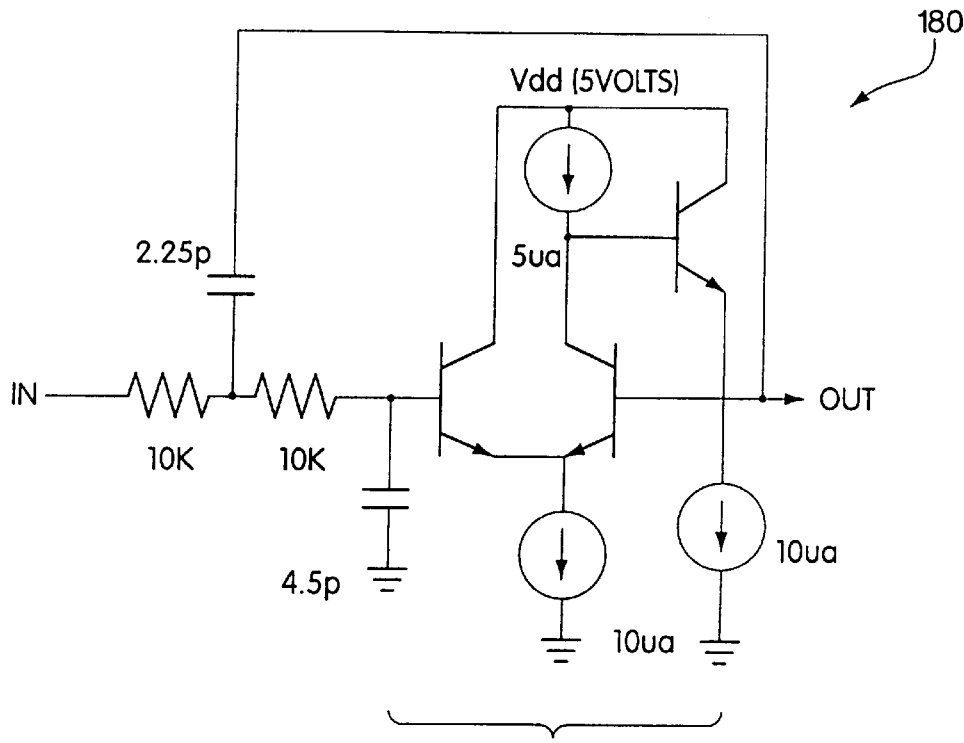
FIGS. 10, 10A and 10B are schematic diagrams of active filters used as delay elements.
Figure 10A:
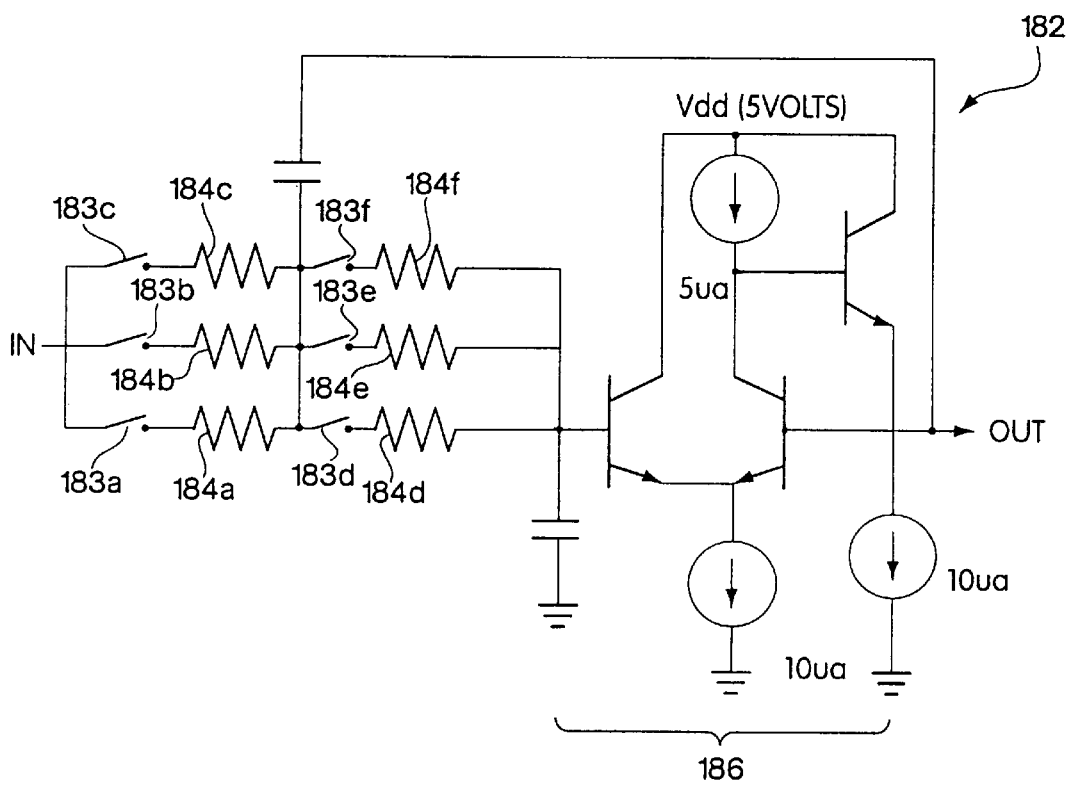
Figure 10B:
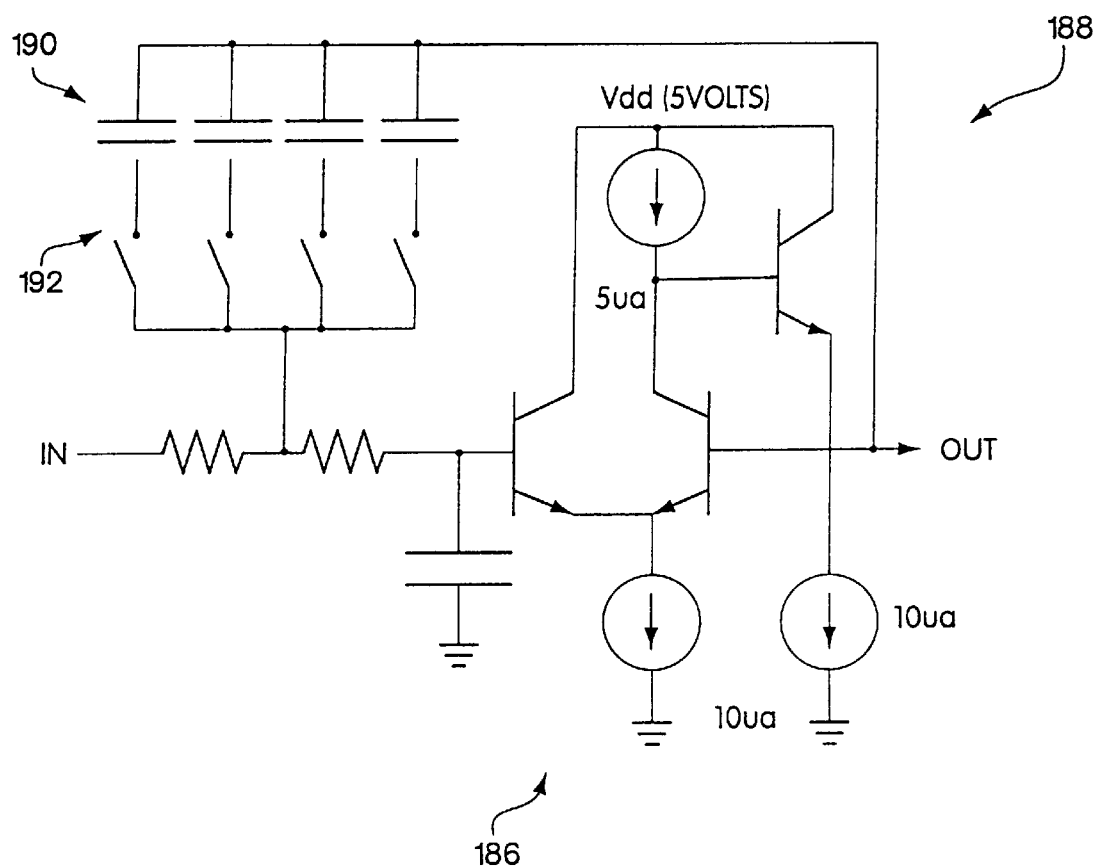

Referring to FIGS. 10, 10A and 10B, in another embodiment, the delay elements (for example shown in FIGS. 6, 7, 8 or 8A) are Sallen and Key implementations of 2-pole active filters 180, 182 and 188. Two-pole active filter 180 may be used in summing delay line 100 or delay lines 125 or 145. Active filter 180 produces a 50 nsec delay at a 5 MHz bandwidth.

Active filters 182 and 188 provide programmable delays and may replace delay lines $118_1$, $118_2$ and $118_R$ in intra-group receive processor 115 (FIG. 7). Active filter 182 provides programmable delay by using a set of resistors 184a through 184f connected to a unity gain buffer 186 by switches 183a through 183f. Alternatively, active filter 188 provides programmable delay values by using a set of capacitors 190 connected to a unity gain buffer 186 by a set of switches 192. Depending on the selected switch the filter's impedance changes that in turn changes the phase response (i.e., the delay). There are several other filter topologies that can be used as delay elements (See, for example, Y. P. Tsvidis and J. O. Voorman "Integrated continuous-time filters" IEEE Press, 1993).

Figure 11:
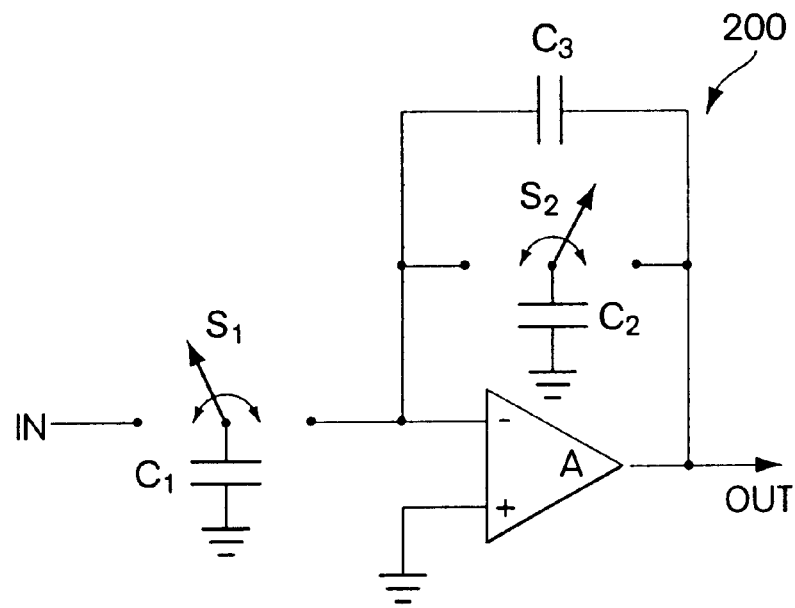
FIGS. 11 and 11A are schematic diagrams of switched capacitor filters used as delay elements.
Figure 11A:
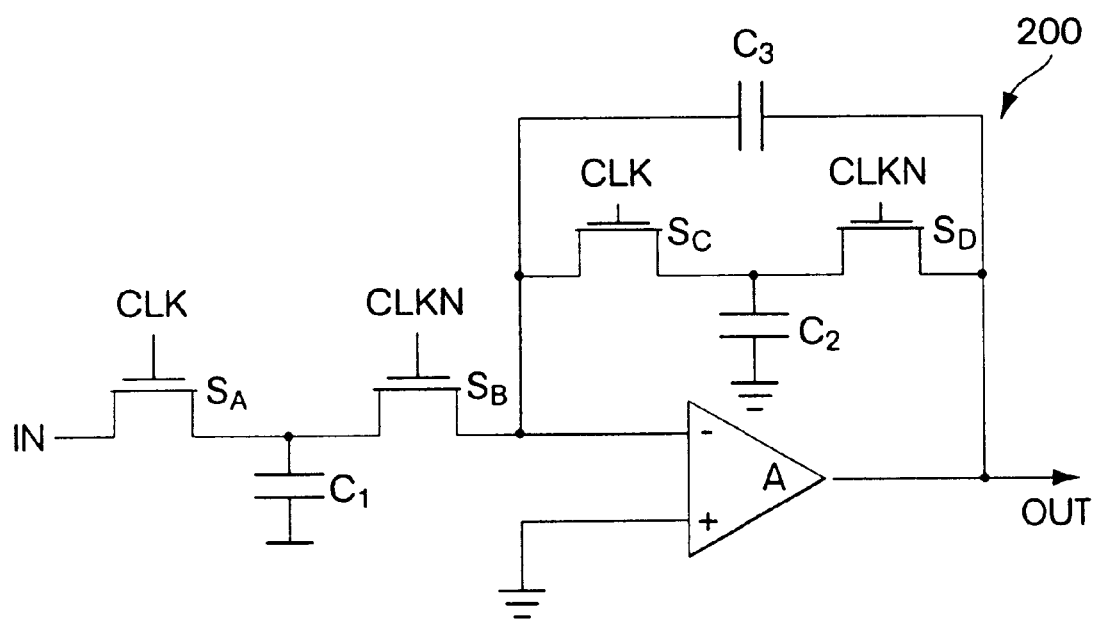

Referring to FIGS. 11 and 11A, in another embodiment, the delay element is a switched capacitor filter 200. Switched-capacitor filter 200 includes capacitors $C_1$, $C_2$, and $C_3$, switches $S_1$ and $S_2$, and an op-amp A arranged as an integrator. Single pole double throw switches $S_1$ and $S_2$ can operate at more than twice the ultrasound center frequency, for example, 10 MHz. As shown in FIG. 11A, switches $S_1$ and $S_2$ may be implemented as MOSFETs $S_A$, $S_B$, $S_C$, and $S_D$. The switching signals CLK and CLKN are derived from a non-overlapping two phase clock of a selected frequency. The delay value can be changed either by using different capacitor values, or by using different clock frequencies. Since these delay elements do not use resistors, their power consumption is relatively low. There are several other filter topologies that can be used (see, for example, M. E. Van Valkenburg "Analog Filter Design" CBS college publishing 1982).

Figure 12:
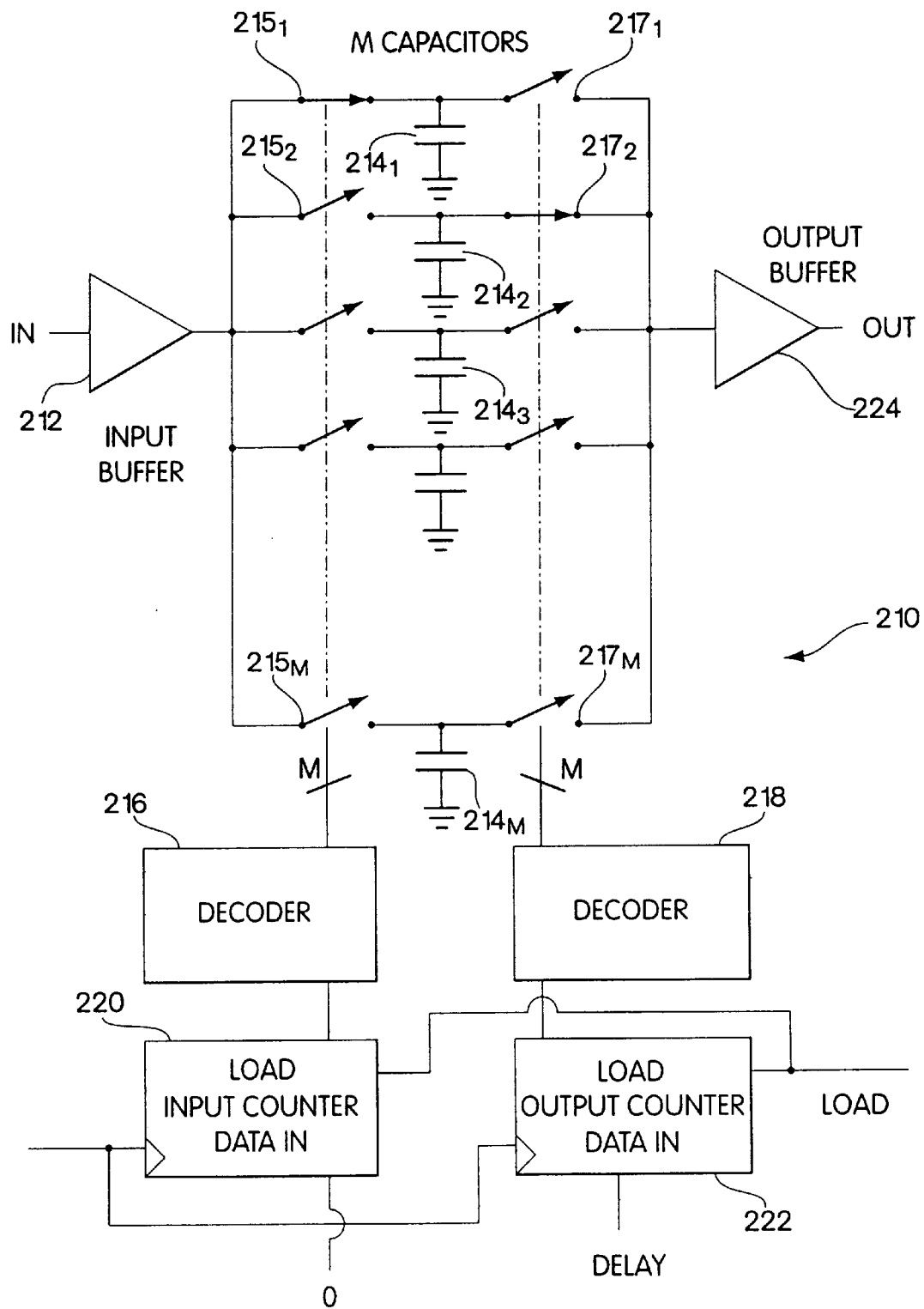
FIG. 12 shows diagrammatically an analog random access memory element used as a programmable delay element.

Referring to FIG. 12, in another embodiment, an analog random access memory (RAM) device 210 is used as a programmable delay element. RAM device 210 includes a group of M storage capacitors $214_1$, $214_2$, ..., $214_M$ for storing M input sample signals using decoders 216 and 218 connected to input switches $215_1$, $215_2$, ..., $215_M$ and output switches $217_1$, $217_2$, ..., $217_M$, respectively. An input buffer 212 receives a transducer signal that is then sent by input switch $215_i$ controlled by decoder 216 to storage capacitor $214_i$. Decoder 218 coupled to output switch $217_i$ samples the individual capacitor charges at delay times determined by the difference in timing between an input counter 220 and an output counter 222. Thus, the transducer signals are delayed by selected delay times as they are transferred from input buffer 212 to an output buffer 224. The analog RAM device may use only a single capacitor for delaying the ultrasound transducer signal in order to reduce the noise and signal distortion.

Figure 12A:
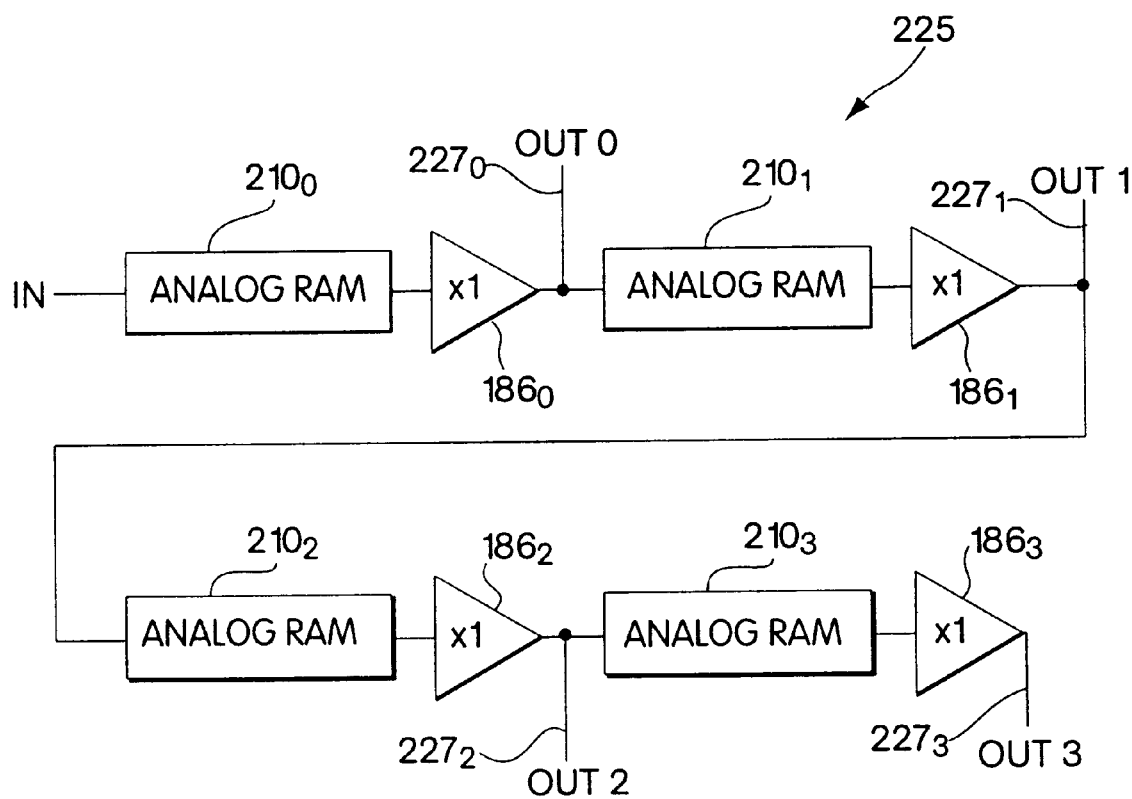
FIG. 12A shows diagrammatically an implementation of the programmable delay line that uses analog random access memory elements.

Another, currently preferred, embodiment uses the analog RAMs in a delay line similar to output delay line 170. FIG. 12A shows diagrammatically a programmable delay line 225, which includes analog RAMs $210_0$, $210_1$, $210_2$ and $210_3$, unity gain buffers $186_0$, $186_1$, $186_2$ and $186_3$, and a set of output taps $227_0$, $227_1$, $227_2$ and $227_3$. Preferably, each analog RAM includes two storage capacitors $214_i$, shown in FIG. 12. Delay line 225 is controlled by a complementary clock signals CLK and CLKN, wherein the CLK frequency is two times the ultrasound RF frequency. Output taps 227, are located every ¼ of the RF period.

Figure 13:
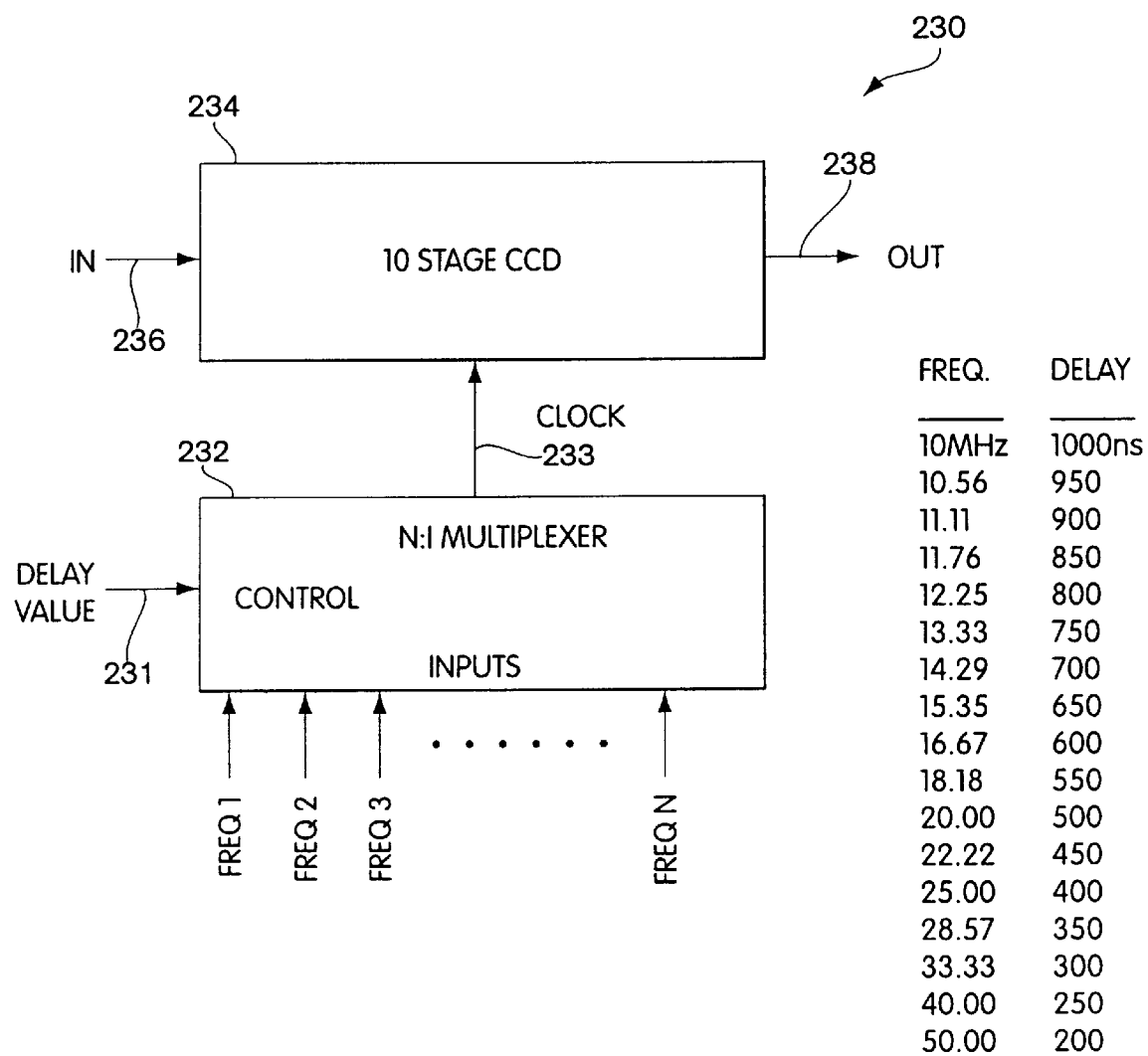
FIG. 13 shows diagrammatically a charge coupled device that can be used as a programmable delay element or a programmable delay line.

Referring to FIG. 13, in another embodiment the programmable delay element is implemented as a charge coupled device (CCD) 230, which includes a chain of capacitors and field effect transistors connected in series. The charge coupled device may be used as a delay element or a delay line. CCD line 230 includes an N:1 multiplexor 232, which provides clock signals to a 10 stage CCD 234. CCD 234 receives the transducer signal at an input 236 and passes the corresponding charge from one capacitor to another each clock period until it reaches an output 238. The total delay required to pass through the CCD is determined by the number of stages and the clock frequency. The delay time is controlled by changing the clock frequency, as shown in Table 1. Multiplexor 232 receives a set of frequencies and provides the appropriate clock frequency (233) to CCD 234 based on a delay value received by a control input 231. The device includes several filters that eliminate clock feed-through across a range of possible clock frequencies.

TABLE 1

| Frequency [MHz] | 10 | 10.56 | 11.11 | 11.76 | 12.25 | 13.33 | 14.29 | 15.35 | 16.67 | 18.18 |
|---|---|---|---|---|---|---|---|---|---|---|
| Delay [nsec] | 1000 | 950 | 900 | 850 | 800 | 750 | 700 | 650 | 600 | 550 |
| Frequency [MHz] | 20.20 | 22.22 | 25.00 | 28.57 | 33.33 | 40.00 | 50.00 | | | |
| Delay [nsec] | 500 | 450 | 400 | 350 | 300 | 250 | 200 | | | |

Figure 13A:
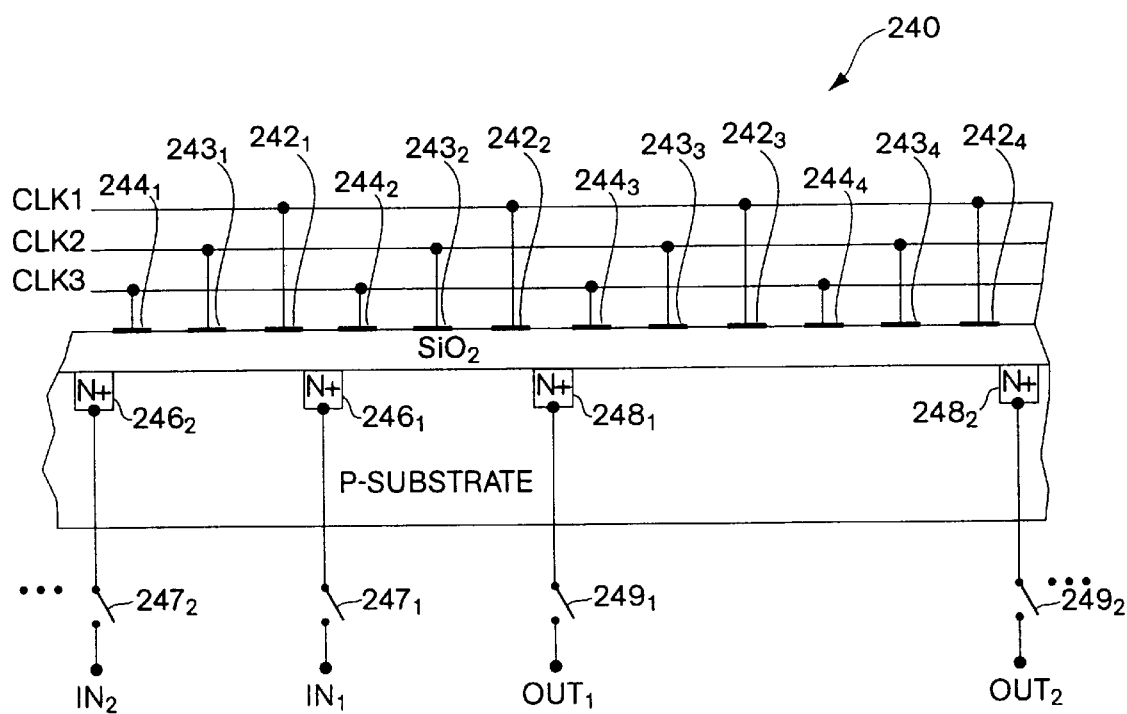
FIG. 13A shows diagrammatically an implementation of the tapped delay line that uses charge coupled devices.

FIG. 13A shows diagrammatically an implementation of the tapped delay line that uses charge coupled devices. A tapped delay line 240 includes a row of closely spaced metallic electrodes $242_1$, $242_2$, ..., $243_1$, $243_2$, ..., and $244_1$, $244_2$, ..., deposited on an $SiO_2$ insulator and several $N^+$ regions $246_1$, $246_2$, ..., and $248_1$, $248_2$, ... located in a P-type substrate. $N^+$ regions $246_1$, $246_2$, ... are connected to input taps $IN_1$, $IN_2$, ... by switches $247_1$, $247_2$, ... $N^+$ regions $248_1$, $248_2$, are connected to output taps $OUT_1$, $OUT_2$, ... by switches $249_1$, $249_2$, ... Electrodes $242_1$, $242_2$, ..., $243_1$, $243_2$, ..., and $244_1$, $244_2$, ... are connected to a three-phase clock $CLK_1$, $CLK_2$ and $CLK_3$ arranged to transfer longitudinally the charge accumulated under the electrodes. Delay line 240 receives the ultrasound transducer signal at input taps $IN_1$, $IN_2$, ... and provides the delayed signal at output taps $OUT_1$, $OUT_2$, ... The delay time depends on the clock frequency and the location of the input and output taps. The description of standard CCDs is provided in "Charge Coupled Devices and Their Application", Beynon et al., McGraw Hill, 1980.

Referring to FIG. 2, the imaging system includes system controller 52 with a digital control circuit for providing the delay values to the intra-group transmit and receive processors and the transmit and receive beamformers, as shown diagrammatically by data buses 53 through 56. The beamformer channels receive "coarse" delay values, and the intra-group processors receive "fine" delay values. The intra-group receive processors cannot be loaded with the delay data while receiving the transducer signals, which are quite weak, because the digital noise, arising from the loading of the delay data, would swamp the weak signals. Therefore, the delay data for each of the 3000 transducer elements must be loaded prior to transmitting each acoustic line. Each element needs about 4 bits of delay data; this corresponds to 12,000 bits of control information, which must be loaded prior to each transmit event. To operate at a high frame rate, the control information has to be loaded in about 10 microseconds; this requires about 75 MHz clock to load 12,000 bits over 16 serial lines in 10 microseconds. While this high rate is possible, there are several ways to reduce this loading rate depending on the mode of operation.

In one embodiment, the digital control circuit provides the same delay profile to all intra-group receive processors. Thus, the intra-group processors can have the delay data loaded in parallel by providing one delay profile to all intra-group processors. The control circuitry loads the delay data to all intra-group processors over a serial line. For example, a processor with 25 elements is loaded over a single serial line clocked at 10 MHz in about 10 microseconds. The intra-group processors steer the acoustic beams by applying the same steering angle to all processors. The intra-group processors loaded with the identical delay profile cannot, however, focus the acoustic beam. Thus, in this embodiment, an acoustic lens may need to be used for focussing.

In another embodiment, the intra-group processors are used for both steering and focussing. The control circuitry provides the steering angle delay data to each intra-group processor. Each processor receives delay data that steers the receive beam at a slightly different angle to achieve focussing. To reduce the loading rate, the delay data for each element is calculated within each intra-group processor by using several adders, as shown in FIG. 14.

Figure 14:
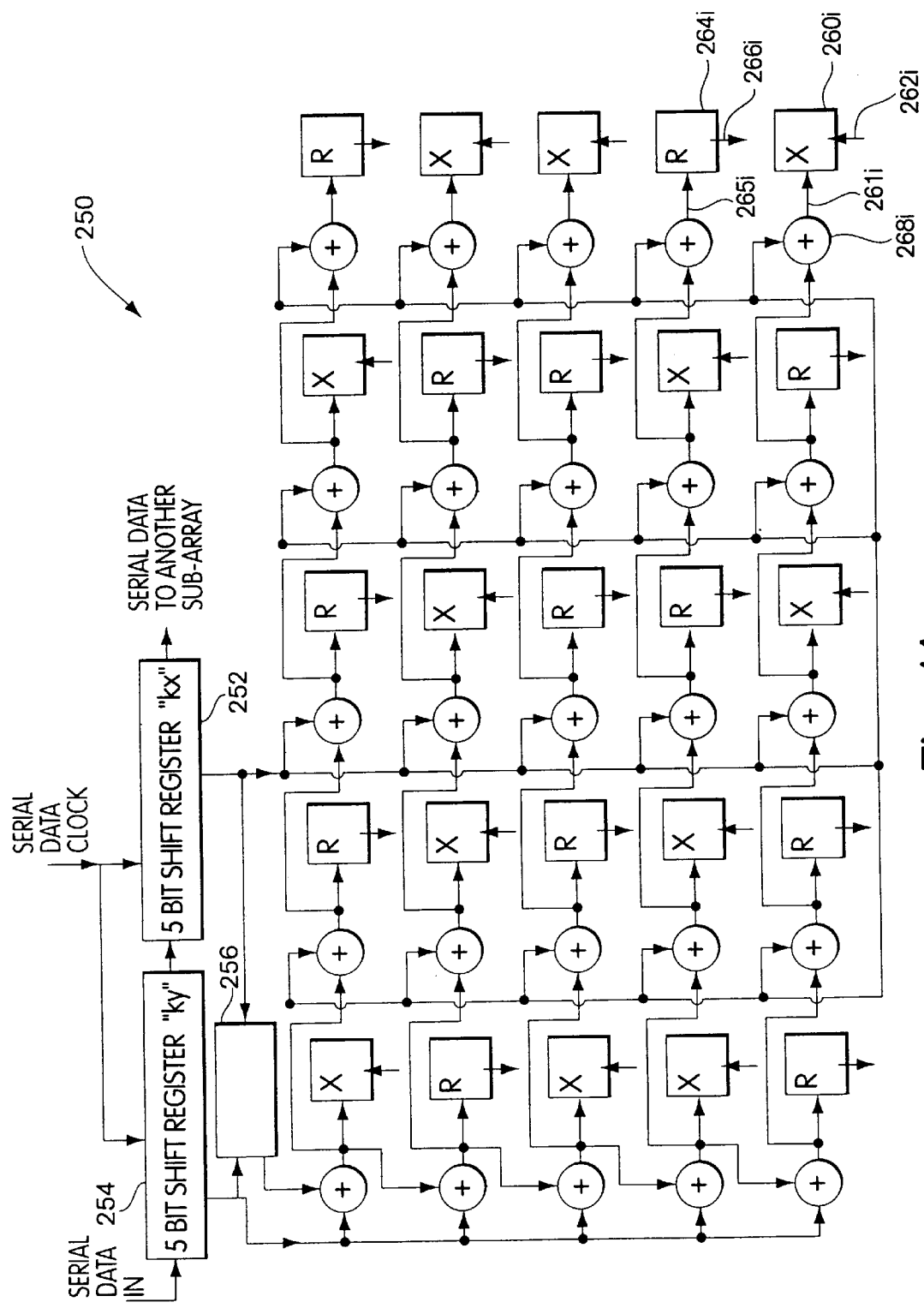
FIG. 14 shows diagrammatically a control circuit for transducer sub-arrays that are connected to an intra-group transmit processor and an intra-group receive processor shown diagrammatically in FIG. 2.

FIG. 14 shows diagrammatically a control circuit 250 used for a 5×5 cell sub-array. This sub-array includes 12 transmit cells connected to an intra-group transmit processor and 13 receive cells connected to an intra-group receive processor. The control circuit includes a shift register 252 for holding an incremental x value, a shift register 254 for holding an incremental y value, and an initial value register 256. Incremental x and y values are directly related to the steering angles in the two-dimensional image plane. Each transmit cell 260, (labeled with an X) includes a transmit transducer and the transmit circuitry (e.g., a high voltage driver). Each receive cell 264, (labeled with an R) includes a receive transducer, a receive preamplifier, and may include the receive circuitry depending on the type of intra-group processor used. There are 25 summing elements (adder junctions) 268, which provide delay data to all transmit and receive cells. (For simplicity, only the i-th element of all elements is labeled in FIG. 14.) The summing elements are preferably asynchronous with no lookahead carry circuitry in order to save power and circuit area.

A serial bus provides an initial delay value to initial value register 256 and the x and y delay increments to shift registers 252 and 254, respectively. Summing elements 268 provide the appropriate delay values for the transducer elements by adding the initial delay value (or the neighboring delay value) and the x and y delay increments. The delays within the group are approximately linear with respect to the cell position so that the summing element associated with each cell can calculate it's delay by a simple offset from it's neighbor's delay. Transmit cells 260 receive the delay values calculated by summing elements 238 via connections 261. Receive cells 264 receive the delay values calculated by summing elements 268 via connections 265. The delay data is used for steering and focussing.

Also referring to FIG. 3, in one embodiment, transmit cells 260 may also include shift register 66. Transmit cell $260_i$ receives a reference pulse via a connection $262_i$, and the shift register provides one of eight delay values to the level shifters. In another embodiment, shift register 66 is located outside of transmit cell $260_i$ and provides to the cell reference pulses via eight connection lines 262 (only one connection line $262_i$ is shown for simplicity). Digital pulse generator 60 together with shift register 66 generate eight reference transmit pulses of N cycles long and delayed from a transmit trigger pulse by M transmit clock cycles plus eight different additional delays. Referring now to FIG. 3A, in another embodiment, transmit cell $262_i$ includes delay line 80. Transmit cell $262_i$ receives a reference pulse from digital pulse generator 60 via connection $262_i$ and delay line 80 provides the signal to level shifters 74.

After detecting the ultrasound echos, receive cells 264 provide pre-amplified acoustic data to the intra-group receive processor. Also referring to FIG. 6, in one embodiment, if the intra-group processor uses summing delay line 100 each receive cell 264, provides the pre-amplified acoustic data via a single connection $266_i$ to one variable gain cross-point switch 104 located outside of the receive cells. That is, there is only one variable gain cross-point switch receiving the acoustic data from all 13 receive cells 264. In another embodiment using summing delay line 100, each receive cell $264_i$ includes one variable gain cross-point switch with a smaller number of switches than when only one cross-point switch is used for all receive cells 264. Each receive cell $264_i$ has several connections 266 providing the acoustic data to summing delay line 100 (FIG. 6). Now referring to FIG. 7, in another embodiment, each receive cell $264_i$ provides the pre-amplified acoustic data via a single connection 266, to one programmable delay element $118_i$. The intra-group receive processor receives the transducer signal from 13 receive cells 264 and provides the summed signal (122) to one channel of the receive beamformer. Depending on the delay values applied by delay elements $118_i$, echoes scattered from a selected point are summed.

Additional embodiments are within the following claims:

What is claimed is:

1. A phased array acoustic apparatus for imaging a region of interest comprising:

a transmit array including a multiplicity of transducer elements allocated into several transmit sub-arrays;

several intra-group transmit processors, connected to said several transmit sub-arrays, constructed and arranged to generate a transmit acoustic beam directed into a region of interest;

a receive array including a multiplicity of transducer elements;

a receive beamformer including
a multiplicity of processing channels connected to said transducer elements, each said processing channel including a beamformer delay constructed and arranged to synthesize receive beams from said echos by delaying signals received from said transducer elements, and
a beamformer summer constructed and arranged to receive and sum signals from said processing channels; and an image generator constructed and arranged to form an image of said region based on signals received from said receive beamformer.

2. The phased array acoustic apparatus of claim 1 further comprising a controller constructed and arranged to provide simultaneously a transmit delay profile to said intra-group transmit processors, said transmit delay profile including signal delay values associated with said transmit transducer elements connected to one of said intra-group transmit processors.

3. The phased array acoustic apparatus of claim 1 further comprising a controller constructed and arranged to provide a transmit number to each said intra-group transmit processor, each said intra-group transmit processor including at least one delay processor constructed and arranged to calculate from said transmit number transmit delay values associated with said transmit transducer elements of said intra-group transmit processor.

4. The phased array acoustic apparatus of claim 3 wherein said delay processors are adders.

5. The phased array acoustic apparatus of claim 1 wherein said intra-group transmit processors include shift registers constructed and arranged to generate pulses with selected delay values.

6. The phased array acoustic apparatus of claim 1 wherein said intra-group transmit processors include multiplexers constructed and arranged to select one of several delay signals used to excite said transmit transducer elements.

7. The phased array acoustic apparatus of claim 1 wherein said intra-group transmit processors include programmable delay lines.

8. The phased array acoustic apparatus of claim 7 wherein said programmable delay line includes dual clock flip-flops.

9. The phased array acoustic apparatus of claim 1 further comprising a handle positionable near said region of interest and constructed to accommodate said transmit transducer elements, said intra-group transmit processors being constructed in an integrated form to be placed within said handle.

10. The phased array acoustic apparatus of claim 1 further comprising
   a handle positionable near said region of interest and constructed to accommodate said transmit transducer elements, and
   a connector constructed to accommodate said intra-group transmit processors being constructed in an integrated form.

11. A phased array acoustic apparatus for imaging a region of interest comprising:
   a transmit array including a multiplicity of transducer elements;
   a transmit beamformer including several transmit beamformer channels connected to said transducer elements constructed and arranged to generate a transmit acoustic beam emitted into a region of interest;
   a receive array including a multiplicity of transducer elements allocated into several receive sub-arrays;
   several intra-group receive processors connected to said several receive sub-arrays, each said intra-group receive processor being arranged to receive, from said transducer elements of said connected sub-array, transducer signals in response to echoes from said transmit acoustic beam, each said intra-group receive processor including
      active analog filter elements forming delay elements arranged to delay said received transducer signals, and
      a summing element constructed to receive said delayed transducer signal and sum said delayed transducer signals;
   a receive beamformer including
      several processing channels connected to said several intra-group receive processors, each said processing channel including a beamformer delay constructed and arranged to synthesize receive beams from said echos by delaying signals received from said intra-group receive processor, and
      a beamformer summer constructed and arranged to receive and sum signals from said processing channels; and
   an image generator constructed and arranged to form an image of said region based on signals received from said receive beamformer.

12. The phased array acoustic apparatus of claim 11 further comprising a controller constructed and arranged to provide simultaneously a receive delay profile to said intra-group receive processors, said receive delay profile including signal delay values associated with said receive transducer elements connected to one of said intra-group receive processors.

13. The phased array acoustic apparatus of claim 11 further comprising a controller constructed and arranged to provide a receive number to each said intra-group receive processor, each said intra-group receive processor including at least one delay processor constructed and arranged to calculate from said receive number receive delay values associated with said receive transducer elements of said intra-group receive processor.

14. The phased array acoustic apparatus of claim 13 wherein said delay processors are adders.

15. The phased array acoustic apparatus of claim 11 wherein said active analog filter elements are arranged with several said summing elements to form a summing delay line.

16. The phased array acoustic apparatus of claim 15 wherein said intra-group receive processor also includes a cross point switch constructed and arranged to connect a signal from said receive transducer element to a selected tap of said summing delay line.

17. The phased array acoustic apparatus of claim 16 wherein said cross point switch is constructed and arranged to connect said signal from several of said receive transducer elements to at least one said taps of said summing delay line.

18. The phased array acoustic apparatus of claim 16 wherein said intra-group receive processor also includes a network of fixed gain amplifiers connected to said cross point switch, said network and said cross point switch being arranged to apply a weighted gain to said signal and connect said weighted gain signal to at least one said tap of said summing delay line.

19. The phased array acoustic apparatus of claim 11 wherein said active analog filter elements are arranged with several said summing elements arranged to form a tapped delay line with input taps.

20. The phased array acoustic apparatus of claim 11 wherein said active analog filter elements are arranged to form a tapped delay line with output taps.

21. The phased array acoustic apparatus of claim 20 wherein said tapped delay line includes several said output taps located between said active analog filter elements and further including a multiplexer connected to said output taps and arranged to select one of said output taps and provide an output connected to said processing channel of said receive beamformer.

22. The phased array acoustic apparatus of claim 21 further including at least two multiplexers connected to said output taps, said multiplexers being constructed and arranged to provide a weighted gain signal from said output taps.

23. The phased array acoustic apparatus of claim 11 further comprising a handle positionable near said region of interest and constructed to accommodate said transducer elements, said intra-group receive processors being constructed in an integrated form to be placed within said handle.

24. The phased array acoustic apparatus of claim 11 further comprising
 a handle positionable near said region of interest and constructed to accommodate said transducer elements, and
 a connector constructed to accommodate said intra-group receive processors being constructed in an integrated form.

25. A phased array acoustic apparatus for imaging a region of interest comprising:
 a transmit array including a multiplicity of transducer elements;
 a transmit beamformer including several transmit beamformer channels connected to said transducer elements constructed and arranged to generate a transmit acoustic beam emitted into a region of interest;
 a receive array including a multiplicity of transducer elements allocated into several receive sub-arrays;
 several intra-group receive processors connected to said several receive sub-arrays, each said intra-group receive processor being arranged to receive, from said transducer elements of said connected sub-array, transducer signals in response to echoes from said transmit acoustic beam, each said intra-group receive processor including
  switched capacitor filter elements forming delay elements arranged to delay said received transducer signals, and
  a summing element constructed to receive said delayed transducer signal and sum said delayed transducer signals;
 a receive beamformer including
  several processing channels connected to said several intra-group receive processors, each said processing channel including a beamformer delay constructed and arranged to synthesize receive beams from said echos by delaying signals received from said intra-group receive processor, and
  a beamformer summer constructed and arranged to receive and sum signals from said processing channels; and
 an image generator constructed and arranged to form an image of said region based on signals received from said receive beamformer.

26. The phased array acoustic apparatus of claim 25 further comprising a controller constructed and arranged to provide simultaneously a receive delay profile to said intra-group receive processors, said receive delay profile including signal delay values associated with said receive transducer elements connected to one of said intra-group receive processors.

27. The phased array acoustic apparatus of claim 25 further comprising a controller constructed and arranged to provide a receive number to each said intra-group receive processor, each said intra-group receive processor including at least one delay processor constructed and arranged to calculate from said receive number receive delay values associated with said receive transducer elements of said intra-group receive processor.

28. The phased array acoustic apparatus of claim 27 wherein said delay processors are adders.

29. The phased array acoustic apparatus of claim 25 wherein switched capacitor filter elements are arranged with several said summing elements to form a summing delay line.

30. The phased array acoustic apparatus of claim 29 wherein said intra-group receive processor also includes a cross point switch constructed and arranged to connect a signal from said receive transducer element to a selected tap of said summing delay line.

31. The phased array acoustic apparatus of claim 30 wherein said cross point switch is constructed and arranged to connect said signal from several of said receive transducer elements to at least one said taps of said summing delay line.

32. The phased array acoustic apparatus of claim 30 wherein said intra-group receive processor also includes a network of fixed gain amplifiers connected to said cross point switch, said network and said cross point switch being arranged to apply a weighted gain to said signal and connect said weighted gain signal to at least one said tap of said summing delay line.

33. The phased array acoustic apparatus of claim 25 wherein said switched capacitor filter elements are arranged with several said summing elements arranged to form a tapped delay line with input taps.

34. The phased array acoustic apparatus of claim 25 wherein said switched capacitor filter elements are arranged to form a tapped delay line with output taps.

35. The phased array acoustic apparatus of claim 34 wherein said tapped delay line includes several said output taps located between said switched capacitor filter elements and further including a multiplexer connected to said output taps and arranged to select one of said output taps and provide an output connected to said processing channel of said receive beamformer.

36. The phased array acoustic apparatus of claim 35 further including at least two multiplexers connected to said output taps, said multiplexers being constructed and arranged to provide a weighted gain signal from said output taps.

37. The phased array acoustic apparatus of claim 25 further comprising a handle positionable near said region of interest and constructed to accommodate said transducer elements, said intra-group receive processors being constructed in an integrated form to be placed within said handle.

38. The phased array acoustic apparatus of claim 25 further comprising
 a handle positionable near said region of interest and constructed to accommodate said transducer elements, and
 a connector constructed to accommodate said intra-group receive processors being constructed in an integrated form.

* * * * *